United States Patent
Imoto et al.

(10) Patent No.: US 10,092,496 B2
(45) Date of Patent: Oct. 9, 2018

(54) STICK-SHAPED BASE MATERIAL CONTAINING LIPID PEPTIDE COMPOUND

(71) Applicant: NISSAN CHEMICAL INDUSTRIES, LTD., Tokyo (JP)

(72) Inventors: Takayuki Imoto, Funabashi (JP); Tsubasa Kashino, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/107,960

(22) PCT Filed: Dec. 25, 2014

(86) PCT No.: PCT/JP2014/084384
§ 371 (c)(1),
(2) Date: Jun. 24, 2016

(87) PCT Pub. No.: WO2015/099074
PCT Pub. Date: Jul. 2, 2015

(65) Prior Publication Data
US 2016/0324749 A1    Nov. 10, 2016

(30) Foreign Application Priority Data

Dec. 25, 2013 (JP) ................ 2013-267608
Jun. 30, 2014 (JP) ................ 2014-134784

(51) Int. Cl.

| | | |
|---|---|---|
| A61K 8/64 | (2006.01) | |
| A61K 9/00 | (2006.01) | |
| A61K 9/06 | (2006.01) | |
| A61Q 19/00 | (2006.01) | |
| A61K 8/02 | (2006.01) | |
| A61K 8/34 | (2006.01) | |
| A61K 8/36 | (2006.01) | |
| A61K 8/67 | (2006.01) | |
| A61K 8/86 | (2006.01) | |
| A61K 47/10 | (2017.01) | |
| A61K 47/12 | (2006.01) | |
| A61K 47/18 | (2017.01) | |
| A61K 47/22 | (2006.01) | |

(52) U.S. Cl.
CPC ............. *A61K 8/64* (2013.01); *A61K 8/0229* (2013.01); *A61K 8/345* (2013.01); *A61K 8/361* (2013.01); *A61K 8/676* (2013.01); *A61K 8/86* (2013.01); *A61K 9/0014* (2013.01); *A61K 9/06* (2013.01); *A61K 47/10* (2013.01); *A61K 47/12* (2013.01); *A61K 47/183* (2013.01); *A61K 47/22* (2013.01); *A61Q 19/00* (2013.01); *A61K 47/18* (2013.01); *A61K 2800/87* (2013.01)

(58) Field of Classification Search
CPC .................................................. A61K 8/64
See application file for complete search history.

(56) References Cited

U.S. PATENT DOCUMENTS

| | | | | |
|---|---|---|---|---|
| 8,486,896 B2* | 7/2013 | Miyachi | ............... | A61K 8/042 252/182.12 |
| 8,716,248 B2* | 5/2014 | Miyachi | ............... | A61K 8/042 252/182.12 |
| 8,816,049 B2* | 8/2014 | Miyachi | ............... | C07K 5/1008 530/330 |
| 8,916,682 B2* | 12/2014 | Miyachi | ............... | C07K 5/1008 530/330 |

(Continued)

FOREIGN PATENT DOCUMENTS

| | | |
|---|---|---|
| EP | 0318206 A1 | 5/1989 |
| EP | 2180027 A1 | 4/2010 |

(Continued)

OTHER PUBLICATIONS

Jul. 28, 2017 Office Action issued in European Patent Application No. 14873681.2.
Mar. 17, 2015 Written Opinion of the International Searching Authority issued in International Patent Application No. PCT/JP2014/084384.

(Continued)

*Primary Examiner* — Amber D Steele
(74) *Attorney, Agent, or Firm* — Oliff PLC

(57) ABSTRACT

A solid base material for skin external application has a breaking strength high enough to be used for a stick-shaped base material and the like. A solid base material for skin external application has: a surfactant; water; and a lipid peptide compound including at least one of compounds of Formula (1) and the analogous thereof or pharmaceutically usable salts of the compound:

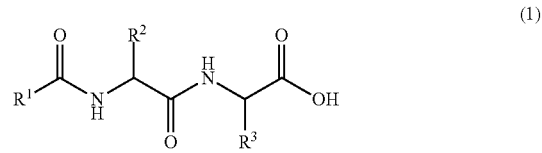

(1)

wherein $R^1$ is a $C_{9-23}$ aliphatic group; $R^2$ is a hydrogen atom, or a $C_{1-4}$ alkyl group that may have a $C_1$ or $C_2$ branched chain; $R^3$ is a —$(CH_2)_n$—X group, where n is a number from 1 to 4, and X is amino group, guanidino group, —$CONH_2$ group, or a 5-membered or 6-membered ring that may have 1 to 3 nitrogen atoms or a condensed heterocycle composed of 5-membered and 6-membered rings that may have 1 to 3 nitrogen atoms.

15 Claims, No Drawings
Specification includes a Sequence Listing.

(56) References Cited

U.S. PATENT DOCUMENTS

| | | | |
|---|---|---|---|
| 8,999,300 B2* | 4/2015 | Iwama | A61K 8/64 424/195.18 |
| 9,265,833 B2* | 2/2016 | Miyamoto | A61K 9/0014 |
| 9,289,496 B2* | 3/2016 | Miyamoto | A61K 9/0014 |
| 9,333,158 B2* | 5/2016 | Miyamoto | A61K 8/046 |
| 9,480,772 B2* | 11/2016 | Goto | A61K 9/0014 |
| 9,561,255 B2* | 2/2017 | Iwama | A61K 8/64 |
| 9,566,218 B2* | 2/2017 | Matsumoto | A61K 8/64 |
| 9,782,331 B2* | 10/2017 | Imoto | A61K 8/04 |
| 2009/0155347 A1 | 6/2009 | Ziegler et al. | |
| 2013/0012686 A1 | 1/2013 | Ziegler et al. | |

FOREIGN PATENT DOCUMENTS

| | | | | |
|---|---|---|---|---|
| EP | 2319894 A1 | 5/2011 | | |
| EP | 2410031 A1 | 1/2012 | | |
| EP | 2638921 A1 | 9/2013 | | |
| EP | 2692335 A1 | 2/2014 | | |
| FR | 2810323 A1 | 12/2001 | | |
| JP | H03-279319 A | 12/1991 | | |
| JP | 2002-516818 A | 6/2002 | | |
| JP | 2012-515196 A | 7/2012 | | |
| WO | 99/23866 A2 | 5/1999 | | |
| WO | 2007/124770 A1 | 11/2007 | | |
| WO | 2011/052613 A1 | 5/2011 | | |
| WO | WO/2011/052613 | * | 5/2011 | A61K 8/64 |
| WO | WO 2011/052613 | * | 5/2011 | A61K 8/64 |
| WO | 2012/063947 A1 | 5/2012 | | |
| WO | 2012/174096 A2 | 12/2012 | | |

OTHER PUBLICATIONS

Mar. 17, 2015 Search Report issued in International Patent Application No. PCT/JP2014/084384.

May 31, 2018 Office Action issued in European Application No. 14873681.2.

* cited by examiner

STICK-SHAPED BASE MATERIAL CONTAINING LIPID PEPTIDE COMPOUND

TECHNICAL FIELD

The present invention relates to a solid base material for skin external application, containing a lipid peptide compound, preferably a stick-shaped base material, and relates to an aqueous composition that contains a lipid peptide compound and is useful as a premix raw material for the solid base material for skin external application.

BACKGROUND ART

Aqueous solid compositions give a refreshing feeling at the time of application to skin and the like and give a less sticky feeling and a smoother and drier feeling after use than oleaginous solid compositions, and therefore, various goods containing aqueous solid compositions for cosmetics and the like have been proposed and put on the market.

As aqueous solid compositions, an oil-in-water type solid cosmetic for makeup containing water, fatty acid soap, oil, and powder (Patent Document 1), and a stick-shaped aqueous cosmetic (Patent Document 2) containing alkyl and/or alkenyl oligo glycoside, an oleaginous substance, and a nonionic emulsifier have been conventionally proposed.

Furthermore, examples of aqueous solid compositions include aqueous gel compositions. As additives for obtaining the aqueous gels, various compounds, such as a polymer gelator and a low molecular weight gelator, have been proposed. In recent years, for example, a low molecular weight lipid peptide gelator that has a high level of living body safety and is expected to be applied to, for example, a biomedical material has been proposed.

PRIOR ART DOCUMENTS

Patent Documents

Patent Document 1: Japanese Patent Application Publication No. H03-279319 (JP 3-279319 A)
Patent Document 2: Japanese Translation of PCT International Application Publication No. 2002-516818 (JP 2002-516818 A)

SUMMARY OF THE INVENTION

Problem to be Solved by the Invention

An aqueous gel to be obtained using the above-mentioned low molecular weight lipid peptide gelator has a relatively low breaking strength, and therefore it has been difficult to apply the aqueous gel to a product requiring a certain level of strength for use, for example, a stick-shaped solid base material for skin external application.

In view of the above-mentioned situations, it is an object of the present invention to provide a solid base material for skin external application that has a breaking strength high enough to be used for a stick-shaped base material and the like.

Means for Solving the Problem

As a result of intensive studies in order to solve the problem, the inventors of the present invention have found that, when a hydrogel is formed of water and a lipid peptide compound (gelator) including a low molecular weight lipid peptide or a pharmaceutically usable salt thereof, a 1,2-alkanediol or glycerol as a solubilizer for the lipid peptide compound and furthermore a surfactant are added, whereby a gel having a much higher breaking strength than a conventional gel is achieved, and can be suitably used as a base material for skin external application, particularly a stick-shaped base material, and have completed the present invention.

Specifically, the present invention relates to, as a first aspect, a solid base material for skin external application, the solid base material comprising a surfactant, water, and a lipid peptide compound including at least one of compounds of Formulae (1) to (3) or pharmaceutically usable salts of the compound.

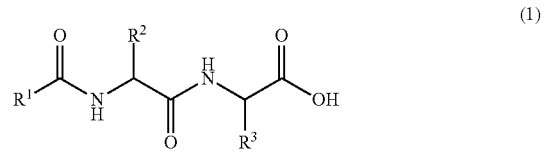

(1)

(where $R^1$ is a $C_{9-23}$ aliphatic group; $R^2$ is a hydrogen atom, or a $C_{1-4}$ alkyl group that may have a $C_1$ or $C_2$ branched chain; and $R^3$ is a —$(CH_2)_n$—X group, where n is a number from 1 to 4, and X is amino group, guanidino group, —$CONH_2$ group, or a 5-membered or 6-membered ring that may have 1 to 3 nitrogen atoms or a condensed heterocycle composed of 5-membered and 6-membered rings that may have 1 to 3 nitrogen atoms.)

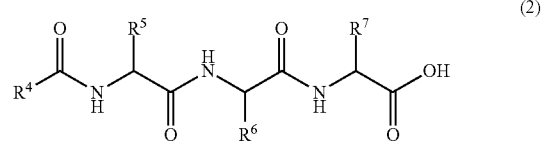

(2)

(where $R^4$ is a $C_{9-23}$ aliphatic group; $R^5$ to $R^7$ are each independently a hydrogen atom, a $C_{1-4}$ alkyl group that may have a $C_1$ or $C_2$ branched chain, or a —$(CH_2)_n$—X group, where n is a number from 1 to 4, and X is amino group, guanidino group, —$CONH_2$ group, or a 5-membered or 6-membered ring that may have 1 to 3 nitrogen atoms or a condensed heterocycle composed of 5-membered and 6-membered rings that may have 1 to 3 nitrogen atoms.)

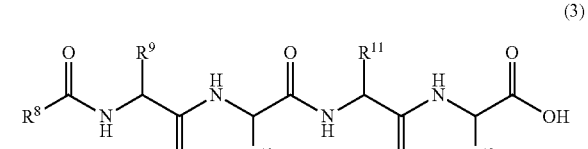

(3)

(where $R^8$ is a $C_{9-23}$ aliphatic group; $R^9$ to $R^{12}$ are each independently a hydrogen atom, a $C_{1-4}$ alkyl group that may have a $C_1$ or $C_2$ branched chain, or a —$(CH_2)_n$—X group, where n is a number from 1 to 4, and X is amino group, guanidino group, —$CONH_2$ group, or a 5-membered or 6-membered ring that may have 1 to 3 nitrogen atoms or a condensed heterocycle composed of 5-membered and 6-membered rings that may have 1 to 3 nitrogen atoms.)

The present invention relates to, as a second aspect, the solid base material for skin external application according to the first aspect, the solid base material further comprising a 1,2-alkanediol or glycerol.

The present invention relates to, as a third aspect, the solid base material for skin external application according to the first aspect or the second aspect, the solid base material further comprising at least one fatty acid.

The present invention relates to, as a fourth aspect, the solid base material for skin external application according to any one of the first aspect to the third aspect, the solid base material further comprising at least one oleaginous base.

The present invention relates to, as a fifth aspect, the solid base material for skin external application according to any one of the first aspect to the fourth aspect, the solid base material further comprising at least one organic acid.

The present invention relates to, as a sixth aspect, the solid base material for skin external application according to any one of the first aspect to the fifth aspect, in which the surfactant is at least one selected from the group consisting of ethylene glycol alkyl ether, phospholipid, polyglycerol fatty acid esters, and polyoxyethylene polyoxypropylene alkyl ether.

The present invention relates to, as a seventh aspect, the solid base material for skin external application according to any one of the third aspect to the sixth aspect, in which the fatty acid is stearic acid.

The present invention relates to, as an eighth aspect, the solid base material for skin external application according to any one of the fifth aspect to the seventh aspect, in which the organic acid is ascorbic acid.

The present invention relates to, as a ninth aspect, the solid base material for skin external application according to any one of the first aspect to the eighth aspect, the solid base material further comprising polyethylene glycol.

The present invention relates to, as a tenth aspect, the solid base material for skin external application according to any one of the first aspect to the ninth aspect, the solid base material being used for cosmetics or pharmaceuticals.

The present invention relates to, as an eleventh aspect, the solid base material for skin external application according to any one of the first aspect to the tenth aspect, the solid base material having the shape of a stick.

The present invention relates to, as a twelfth aspect, an aqueous composition comprising a surfactant, water, and a lipid peptide compound including at least one of compounds of the above-mentioned Formulae (1) to (3) or pharmaceutically usable salts of the compound.

The present invention relates to, as a thirteenth aspect, the aqueous composition according to the twelfth aspect, the aqueous composition further comprising a 1,2-alkanediol or glycerol.

The present invention relates to, as a fourteenth aspect, the aqueous composition according to the twelfth aspect or the thirteenth aspect, the aqueous composition further comprising at least one fatty acid.

The present invention relates to, as a fifteenth aspect, the aqueous composition according to any one of the twelfth aspect to the fourteenth aspect, in which the surfactant is at least one selected from the group consisting of ethylene glycol alkyl ether, phospholipid, polyglycerol fatty acid esters, and polyoxyethylene polyoxypropylene alkyl ether.

The present invention relates to, as a sixteenth aspect, the aqueous composition according to any one of the twelfth aspect to the fifteenth aspect, the aqueous composition being a premix for the preparation of a solid base material for skin external application.

The present invention relates to, as a seventeenth aspect, a method for producing the solid base material for skin external application according to the first aspect, the method comprising the steps of:

heating the aqueous composition according to any one of the twelfth aspect to the sixteenth aspect at room temperature or higher and less than 100° C.;

adding the heated aqueous composition to an aqueous phase heated at room temperature or higher and less than 100° C., followed by mixing; and cooling the resultant mixture to form a gel.

The present invention relates to, as an eighteenth aspect, the production method according to the seventeenth aspect, in which the aqueous phase contains at least one oleaginous base.

The present invention relates to, as a nineteenth aspect, the production method according to the seventeenth aspect, in which the aqueous phase contains polyethylene glycol.

The present invention relates to, as a twentieth aspect, a method for producing the solid base material for skin external application according to the fifth aspect, the method comprising the steps of:

heating the aqueous composition according to any one of the twelfth aspect to the sixteenth aspect at room temperature or higher and less than 100° C.;

adding the heated aqueous composition to an aqueous phase heated at room temperature or higher and less than 100° C., followed by mixing;

cooling the resultant mixture to form a gel; and adding a mixed solution of water and an organic acid to the mixture during the cooling process, followed by further mixing.

The present invention relates to, as a twenty first aspect, the production method according to the twentieth aspect, in which the aqueous phase contains at least one oleaginous base.

Effects of the Invention

The present invention provides a solid base material for skin external application that has a higher strength than conventional aqueous gel base materials, and furthermore, has a low acidity, that is, a pH of about 5.

Furthermore, the present invention provides a solid base material for skin external application that is a gel base material capable of both having a high water content of approximately 90% by mass and containing an oleaginous component at the same time.

The lipid peptide compound to be contained in the solid base material for skin external application of the present invention is an artificial low molecular weight compound that is composed of only lipid and peptide, thereby having an extremely high level of safety. Furthermore, the compound allows an aqueous gel to be formed without using a cross linking agent or the like that is necessary for forming a conventional synthetic polymer gel, and therefore, there arises no problem that an unreacted substance, such as an unreacted cross linking agent, remains in a solid base material for skin external application to be obtained.

Each principal ingredient to be contained as an additive in the solid base material for skin external application of the present invention is a general-purpose additive as an additive in food, cosmetics, and pharmaceutical products.

That is, the solid base material for skin external application of the present invention has a high level of living body safety, and, in particular, from the viewpoint of high safety required for a material for medical use, cosmetic use, or the like, the solid base material is extremely useful in the above-mentioned uses.

Furthermore, the solid base material for skin external application of the present invention is expected to be a base material that gives a refreshing feeling, is neither broken nor deformed, and spreads well when applied to a human skin or the like, and therefore, the solid base material is extremely useful as a base material for cosmetics or pharmaceutical products, in particular, as a stick-shaped base material.

Furthermore, the present invention provides an aqueous composition suitable as a premix raw material for the solid base material for skin external application.

By using the aqueous composition, the present invention provides a solid base material for skin external application that is in the form of gel and has a strength required as a stick-shaped base material, in particular, even in the case where a large amount of an organic acid such as ascorbic acid is contained in the solid base material.

MODES FOR CARRYING OUT THE INVENTION

The present invention relates to a solid base material for skin external application, the solid base material comprising: a surfactant, water, and a lipid peptide compound including at least one of compounds of Formulae (1) to (3) or pharmaceutically usable salts thereof, the solid material base further comprising a 1,2-alkanediol or glycerol, a fatty acid, an oleaginous base, an organic acid, polyethylene glycol, or other additives, if desired.

The present invention also relates to an aqueous composition that comprises the surfactant, water, and the lipid peptide compound, and, if desired, comprises a 1,2-alkanediol or glycerol, and a fatty acid, and may further comprise an oleaginous base, an organic acid, polyethylene glycol, and other additives.

The solid base material for skin external application of the present invention is suitable for cosmetics or pharmaceutical products, and in particular, can be applied as a stick-shaped base material. Note that, in the present invention, a stick-shaped base material refers to a bar-shaped base material that has a strength enough to maintain the shape of a bar and to be applicable to skin, for example. The strength required of a stick-shaped base material is, for example, a breaking strength of $0.4 \times 10^5$ Pa to $8.0 \times 10^5$ Pa, preferably $1.0 \times 10^5$ Pa to $7.0 \times 10^5$ Pa, more preferably $1.0 \times 10^5$ Pa to $6.0 \times 10^5$ Pa.

Hereinafter, each of the ingredients will be described.

[Lipid Peptide Compound]

As the lipid peptide compound to be contained in the solid base material for skin external application or the aqueous composition of the present invention, compounds (lipid peptides) of Formulae (1) to (3) or pharmaceutically usable salts thereof (low molecular weight compounds having a lipid moiety serving as a hydrophobic moiety and a peptide moiety serving as a hydrophilic moiety) may be used.

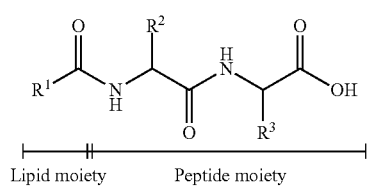

(1)

In Formula (1), $R^1$ is a $C_{9-23}$ aliphatic group, preferably a $C_{11-23}$ linear aliphatic group that may have 0 to 2 unsaturated bonds.

Specific examples of the lipid moiety (acyl group) composed of $R^1$ and a carbonyl group adjacent thereto include lauroyl group, dodecylcarbonyl group, myristoyl group, tetradecylcarbonyl group, palmitoyl group, margaroyl group, oleoyl group, elaidoyl group, linoleoyl group, stearoyl group, vaccenoyl group, octadecylcarbonyl group, arachidoyl group, eicosylcarbonyl group, behenoyl group, elkanoyl group, docosylcarbonyl group, lignoceroyl group, and nervonoyl group, and particularly preferred examples thereof include lauroyl group, myristoyl group, palmitoyl group, margaroyl group, stearoyl group, oleoyl group, elaidoyl group, and behenoyl group.

In Formula (1), $R^2$ included in the peptide moiety is a hydrogen atom, or a $C_{1-4}$ alkyl group that may have a $C_1$ or $C_2$ branched chain.

The $C_{1-4}$ alkyl group that may have a $C_1$ or $C_2$ branched chain refers to an alkyl group that has a $C_{1-4}$ main chain and may have a $C_1$ or $C_2$ branched chain. Specific examples of the $C_{1-4}$ alkyl group include methyl group, ethyl group, n-propyl group, i-propyl group, n-butyl group, i-butyl group, sec-butyl group, and tert-butyl group.

$R^2$ is preferably a hydrogen atom, or a $C_{1-3}$ alkyl group that may have a $C_1$ branched chain, and is more preferably a hydrogen atom.

The $C_{1-3}$ alkyl group that may have a $C_1$ branched chain refers to an alkyl group that has a $C_{1-3}$ main chain and may have a $C_1$ branched chain. Specific examples of the $C_{1-3}$ alkyl group include methyl group, ethyl group, n-propyl group, i-propyl group, i-butyl group, and sec-butyl group, and preferably methyl group, i-propyl group, i-butyl group, and sec-butyl group.

In Formula (1), $R^3$ is a —$(CH_2)_n$—X group. In the —$(CH_2)_n$—X group, n is a number from 1 to 4; and X is amino group, guanidino group, —$CONH_2$ group, or a 5-membered or 6-membered ring group that may have 1 to 3 nitrogen atoms or a condensed heterocyclic group composed of 5-membered and 6-membered rings that may have 1 to 3 nitrogen atoms.

In the —$(CH_2)_n$—X group serving as $R^3$, X is preferably amino group, guanidino group, carbamoyl group (—$CONH_2$ group), pyrrole group, imidazole group, pyrazole group, or indole group, and more preferably imidazole group. Furthermore, in the —$(CH_2)_n$—X group, n is preferably 1 or 2, more preferably 1.

Accordingly, the —$(CH_2)_n$—X group is preferably aminomethyl group, 2-aminoethyl group, 3-aminopropyl group, 4-aminobutyl group, carbamoylmethyl group, 2-carbamoylethyl group, 3-carbamoylbutyl group, 2-guanidinoethyl group, 3-guanidinobutyl group, pyrrolemethyl group, 4-imidazolemethyl group, pyrazolemethyl group, or 3-indolemethyl group, more preferably 4-aminobutyl group, carbamoylmethyl group, 2-carbamoylethyl group, 3-guanidinobutyl group, 4-imidazolemethyl group, or 3-indolemethyl group, and still more preferably 4-imidazolemethyl group.

Particularly preferred examples of the lipid peptide compound of Formula (1) include the following compounds each formed of a lipid moiety and a peptide moiety (amino acid assembly moiety), where amino acid abbreviations used here are alanine (Ala), asparagine (Asn), glutamine (Gln), glycine (Gly), histidine (His), isoleucine (Ile), leucine (Leu), lysine (Lys), tryptophan (Trp), and valine (Val): lauroyl-Gly-His, lauroyl-Gly-Gln, lauroyl-Gly-Asn, lauroyl-Gly-Trp, lauroyl-Gly-Lys, lauroyl-Ala-His, lauroyl-Ala-Gln, lauroyl-Ala-Asn, lauroyl-Ala-Trp, lauroyl-Ala-Lys; myristoyl-Gly- His, myristoyl-Gly-Gln, myristoyl-Gly-Asn, myristoyl-Gly-Trp, myristoyl-Gly-Lys, myristoyl-Ala-His, myristoyl-Ala-Gln, myristoyl-Ala-Asn, myristoyl-Ala-Trp, myristoyl-Ala-Lys; palmitoyl-Gly-His, palmitoyl-Gly-Gln, palmitoyl-Gly-Asn, palmitoyl-Gly-Trp, palmitoyl-Gly-Lys, palmitoyl-Ala-His, palmitoyl-Ala-Gln, palmitoyl-Ala-Asn, palmitoyl-Ala-Trp, palmitoyl-Ala-Lys; and stearoyl-Gly-His, stearoyl-Gly-Gin, stearoyl-Gly-Asn, stearoyl-Gly-Trp, stearoyl-Gly-Lys, stearoyl-Ala-His, stearoyl-Ala-Gln, stearoyl-Ala-Asn, stearoyl-Ala-Trp, stearoyl-Ala-Lys.

The most preferred lipid peptide compounds are lauroyl-Gly-His, lauroyl-Ala-His, myristoyl-Gly-His, myristoyl-Ala-His; palmitoyl-Gly-His, palmitoyl-Ala-His; and stearoyl-Gly-His, stearoyl-Ala-His.

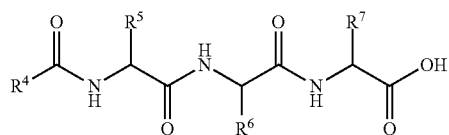

(2)

In Formula (2), $R^4$ is a $C_{9-23}$ aliphatic group, and preferred specific examples of $R^4$ include the same groups as defined by the above-mentioned $R^1$.

In Formula (2), $R^5$ to $R^7$ are each independently a hydrogen atom, a $C_{1-4}$ alkyl group that may have a $C_1$ or $C_2$ branched chain, or a —$(CH_2)_n$—X group, and at least one of $R^5$ to $R^7$ is a —$(CH_2)_n$—X group. n is a number from 1 to 4, and X is amino group, guanidino group, —$CONH_2$ group, or a 5-membered or 6-membered ring group that may have 1 to 3 nitrogen atoms or a condensed heterocyclic group composed of a 5-membered and 6-membered rings that may have 1 to 3 nitrogen atoms. Here, preferred specific examples of $R^5$ to $R^7$ include the same groups as defined by the above-mentioned $R^2$ and $R^3$.

Preferred examples of the lipid peptide compound of Formula (2) include the following compounds each formed of a lipid moiety and a peptide moiety (amino acid assembly moiety): myristoyl-Gly-Gly-His, myristoyl-Gly-Gly-Gln, myristoyl-Gly-Gly-Asn, myristoyl-Gly-Gly-Trp, myristoyl-Gly-Gly-Lys, myristoyl-Gly Ala-His, myristoyl-Gly-Ala-Gln, myristoyl-Gly-Ala-Asn, myristoyl-Gly-Ala-Trp, myristoyl-Gly-Ala-Lys, myristoyl-Ala-Gly-His, myristoyl-Ala-Gly-Gln, myristoyl-Ala-Gly-Asn, myristoyl-Ala-Gly-Trp, myristoyl-Ala-Gly-Lys, myristoyl-Gly-His-Gly, myristoyl-His-Gly-Gly, palmitoyl-Gly-Gly-His, palmitoyl-Gly-Gly-Gln, palmitoyl-Gly-Gly-Asn, palmitoyl-Gly-Gly-Trp, palmitoyl-Gly-Gly-Lys, palmitoyl-Gly Ala-His, palmitoyl-Gly-Ala-Gln, palmitoyl-Gly-Ala-Asn, palmitoyl-Gly-Ala-Trp, palmitoyl-Gly-Ala-Lys, palmitoyl-Ala-Gly-His, palmitoyl-Ala-Gly-Gin, palmitoyl-Ala-Gly-Asn, palmitoyl-Ala-Gly-Trp, palmitoyl-Ala-Gly-Lys, palmitoyl-Gly-His-Gly, and palmitoyl-His-Gly-Gly.

Among them, the most preferred compounds are lauroyl-Gly-Gly-His, myristoyl-Gly-Gly-His, palmitoyl-Gly-Gly-His, palmitoyl-Gly-His-Gly, palmitoyl-His-Gly-Gly, and stearoyl-Gly-Gly-His.

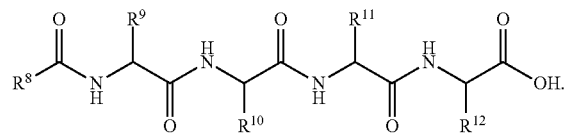

(3)

In Formula (3), $R^8$ is a $C_{9-23}$ aliphatic group, and preferred specific examples of $R^8$ include the same groups as defined by the above-mentioned $R^1$.

In Formula (3), $R^9$ to $R^{12}$ are each independently a hydrogen atom, a $C_{1-4}$ alkyl group that may have a $C^1$ or $C^2$ branched chain, or a —$(CH_2)_n$—X group, and at least one of $R^9$ to $R^{12}$ is a —$(CH_2)_n$—X group. n is a number from 1 to 4, and X is an amino group, a guanidino group, a —$CONH_2$ group, or a 5-membered or 6-membered ring group that may have 1 to 3 nitrogen atoms or a condensed heterocyclic group composed of 5-membered and 6-membered rings that may have 1 to 3 nitrogen atoms. Here, preferred specific examples of $R^9$ to $R^{12}$ include the same groups as defined by the above-mentioned $R^2$ and $R^3$.

Accordingly, particularly preferred examples of the lipid peptide compound of Formula (3) include lauroyl-Gly-Gly-Gly-His (SEQ ID NO: 1), myristoyl-Gly-Gly-Gly-His (SEQ ID NO: 2), palmitoyl-Gly-Gly-Gly-His (SEQ ID NO: 3), palmitoyl-Gly-Gly-His-Gly (SEQ ID NO: 4), palmitoyl-Gly-His-Gly-Gly (SEQ ID NO: 5), palmitoyl-His-Gly-Gly-Gly (SEQ ID NO: 6), and stearoyl-Gly-Gly-Gly-His (SEQ ID NO: 7).

In the present invention, the amount of the lipid peptide compound to be contained is, for example, 1% by mass to 20% by mass, preferably 1% by mass to 10% by mass, and more preferably 4% by mass to 5% by mass with respect to the total mass of an obtained solid base material for skin external application.

In the present invention, the amount of the lipid peptide compound to be contained is, for example, 5% by mass to 20% by mass, and preferably 10% by mass to 20% by mass with respect to the total mass of an obtained aqueous composition.

Note that the lipid peptide compound used in the present invention comprises at least one of compounds (lipid peptide) of Formulae (1) to (3) or pharmaceutically usable salts thereof, and as a hydrogelator, these compounds may be used singly or two or more of them may be used in combination.

[Surfactant]

As a surfactant used in the solid base material for skin external application or the aqueous composition of the present invention, there may be preferably used a compound having a hydrophilic moiety with a betaine structure and a hydrophobic moiety in a molecule (hereinafter, also referred to as a betaine compound), ethylene glycol alkyl ether, a polyglycerol fatty acid ester, or polyoxyethylene polyoxypropylene alkyl ether.

As the above-mentioned betaine compound, there may be preferably used a betaine compound known as an amphoteric surfactant, for example, N-alkyl-N,N-dimethylamino acid betaines, such as lauryl dimethylaminoacetic acid betaine (lauryl betaine); fatty acid amido alkyl-N,N-dimethylamino acid betaines, such as cocamide propyl betaine and lauramide propyl betaine; imidazoline betaines, such as sodium cocoamphoacetate and sodium lauroamphoacetate; alkyl sulfobetaines, such as lauryl hydroxysulfobetaine and alkyl dimethyltaurine; betaine sulfates, such as alkyl dimethylaminoethanol sulfate; and betaine phosphate, such as alkyl dimethylaminoethanol phosphate.

Furthermore, examples of the betaine compound include glycerophospholipids, such as phosphatidylcholine, phosphatidylethanolamine, phosphatidylserine, phosphatidylinositol, phosphatidylglycerol, diphosphatidylglycerol (cardiolipin), and phosphatidic acid; lysoglycerophospholipids, such as lysophosphatidylcholine (lysolecihin), lysophosphatidylethanolamine, lysophosphatidylserine, lysophosphatidylinositol, lysophosphatidylglycerol, and lysophosphatidic acid; sphingophospholipids, such as sphingomyelin; and hydrogenated derivatives of these phospholipids. These phospholipids may be animal- or plant-derived phospholipids, such as soybeans and egg yolks, or may be chemically or enzymatically synthesized phospholipids.

Among the above-mentioned betaine compounds, preferred examples of the betaine compound include lauryl dimethylaminoacetic acid betaine, lauramidopropyl betaine, lauryl hydroxysulfobetaine, stearyl betaine, lysophosphatidylcholine (lysolecithin), lysophosphatidylethanolamine, lysophosphatidylserine, lysophosphatidylinositol, lysophosphatidylglycerol, and lysophosphatidic acid, and more preferred examples thereof include lysophosphatidylcholine (lysolecithin).

Examples of the above-mentioned ethylene glycol alkyl ether include polyoxyethylene alkyl ether, polyoxyethylene lauryl ether, polyoxyethylene palmitoyl ether, and polyoxyethylene stearylether. Furthermore, a commercially available ethylene glycol alkyl ether may be used, and examples of such commercial products include, out of EMULGEN (registered trademark) series and EMANON (registered trademark) series manufactured by Kao Corporation, EMULGEN 102KG, EMULGEN 103, EMULGEN 104P, EMULGEN 105, EMULGEN 106, EMULGEN 108, EMULGEN 109P, EMULGEN 120, EMULGEN 123P, EMULGEN 130K, EMULGEN 147, EMULGEN 150, EMULGEN 210P, EMULGEN 220, EMULGEN 306P, EMULGEN 320P, EMULGEN 350, EMULGEN 404, EMULGEN 408, EMULGEN 409PV, EMULGEN 420, EMULGEN 430, EMULGEN 705, EMULGEN 707, EMULGEN 709, EMULGEN 1108, EMULGEN 1118S-70, EMULGEN 1135S-70, EMULGEN 1150S-60, EMULGEN 4085, EMULGEN 2020G-HA, EMULGEN 2025G, EMANON 1112, EMANON 3199V, EMANON 3299V, EMANON 3299RV, and EMANON 4110. More preferred examples thereof include EMULGEN 103, EMULGEN 104P, EMULGEN 105, EMULGEN 106, EMULGEN 108, EMULGEN 109P, EMULGEN 210P, EMULGEN 306P, EMULGEN 320P, EMULGEN 404, EMULGEN 408, EMULGEN 409PV, EMULGEN 420, EMULGEN 705, EMULGEN 707, EMULGEN 709, EMULGEN 1108, EMULGEN 2020G-HA, EMANON 1112, and EMANON 4110, each manufactured by Kao Corporation. Still more preferred examples of the commercial products include EMULGEN 104P, EMULGEN 105, EMULGEN 106, EMULGEN 108, EMULGEN 210P, EMULGEN 306P, EMULGEN 408, EMULGEN 409PV, EMULGEN 705, EMULGEN 707, EMULGEN 709, EMULGEN 1108, EMULGEN 2020G-HA, EMANON 1112, and EMANON 4110, each manufactured by Kao Corporation. Besides these, also from NIKKOL (registered trademark) series manufactured by Nikko Chemicals Co., Ltd., the commercial product may be suitably selected. Examples of the suitably-selected NIKKOL series product include NIKKOL BT-5, NIKKOL BT-7, NIKKOL BT-9, and NIKKOL BT-12.

Examples of the above-mentioned polyglycerol fatty acid ester include glycerol fatty acid partial esters, such as glyceryl stearate, glyceryl isostearate, glyceryl palmitate, glyceryl myristate, glyceryl oleate, glyceryl cocoate, glycerin mono-cottonseed oil fatty acid esters, glycerin monoerucate, glycerin sesquioleate, glycerin α,α'-oleate pyroglutamate, and glycerin monostearate malate; polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, polyglyceryl-6 distearate, polyglyceryl-10 distearate, polyglyceryl-2 tristearate, polyglyceryl-10 decastearate, polyglyceryl-2 isostearate, polyglyceryl-3 isostearate, polyglyceryl-4 isostearate, polyglyceryl-5 isostearate, polyglyceryl-6 isostearate, polyglyceryl-8 isostearate, polyglyceryl-10 isostearate, polyglyceryl-2 diisostearate (diglyceryl diisostearate), polyglyceryl-3 diisostearate, polyglyceryl-10 diisostearate, polyglyceryl-2 triisostearate, polyglyceryl-2 tetraisostearate, polyglyceryl-10 decaisostearate, polyglyceryl-2 oleate, polyglyceryl-3 oleate, polyglyceryl-4 oleate, polyglyceryl-5 oleate, polyglyceryl-6 oleate, polyglyceryl-8 oleate, polyglyceryl-10 oleate, polyglyceryl-6 dioleate, polyglyceryl-2 trioleate, and polyglyceryl-10 decaoleate.

Examples of the polyoxyethylene polyoxypropylene alkyl ether include EMULGEN (registered trademark) LS-106, EMULGEN LS-110, EMULGEN LS-114, and EMULGEN MS-110, each manufactured by Kao Corporation; and NIKKOL (registered trademark) PBC-31, NIKKOL PBC-33, NIKKOL PBC-34, NIKKOL PBC-41, NIKKOL PBC-44, NIKKOL PBN-4612, NIKKOL PBN-4620, and NIKKOL PBN-4630, each manufactured by Nikko Chemicals Co., Ltd. More preferred examples of polyoxyethylene polyoxypropylene alkyl ether include EMULGEN LS-106, EMULGEN LS-110, EMULGEN LS-114, and EMULGEN MS-110. Still more preferred examples of polyoxyethylene polyoxypropylene alkyl ether include EMULGEN LS-106, EMULGEN LS-110, and EMULGEN MS-110.

As the surfactant used in the present invention, a surfactant having an HLB (Hydrophile-Lipophile Balance) value of 8 to 20 may be preferably used. A surfactant having an HLB value of 8 to 14 may be more preferably used.

Examples of such surfactant include sorbitan isostearate, steareth-8, beheneth-10, laureth-5, ceteth-7, oleth-8, PEG-8 glyceryl isostearate, choleth-10, PEG-10BG isostearate, PEG-30 glyceryl triisostearate, PEG-30 glyceryl triisostearate, PEG-30 glyceryl trioleate, PEG-30 trimethylolpropane triisostearate, PEG-30 hydrogenated castor oil laurate, PEG-30 hydrogenated castor oil PCA isostearate, octyldodeceth-10, PEG-12 dilaurate, sorbeth-40 tetraoleate, polyglyceryl-10 diisostearate, PEG-20 glyceryl diisostearate, PEG-8 isostearate, PEG-10 glyceryl isostearate, PEG-60 hydrogenated castor oil triisostearate, PPG-2-deceth-7, oleth-10, hydrogenated dimer dilinoleth-20, sorbitan cocoate, isosteareth-10, steareth-11, PEG-30 trimethylolpropane trimyristate, PEG-40 hydrogenated castor oil isostearate, PEG-40 hydrogenated castor oil isostearate, PEG-40 hydrogenated castor oil PCA isostearate, laureth-7, isoceteth-10, ceteth-10, PEG-10 isostearate, PEG-10 stearate, PEG-10 oleate, PEG-10 glyceryl stearate, oleth-12, decyltetradeceth-15, choleth-15, PEG-16 dilaurate, PEG-30 hydrogenated castor oil, PEG-40 glyceryl triisostearate, PEG-40 glyceryl trioleate, PEG-40 trimethylolpropane triisostearate, PEG-40 hydrogenated castor oil laurate, and PEG-12 laurate.

In the present invention, the amount of the surfactant to be contained is, for example, 1% by mass to 20% by mass, preferably 1% by mass to 10% by mass, and more preferably 1% by mass to 5% by mass with respect to the total mass of an obtained solid base material for skin external application.

In the present invention, the amount of the surfactant to be contained is, for example, 1% by mass to 20% by mass, preferably 2% by mass to 10% by mass with respect to the total mass of an obtained aqueous composition.

Note that the surfactant used in the present invention is at least one of the above-mentioned surfactants, and these surfactants may be used singly or two or more of them may be used in combination.

[1,2-Alkanediol or Glycerol]

The solid base material for skin external application or the aqueous composition of the present invention may contain a 1,2-alkanediol. The 1,2-alkanediol has the function of promoting the solubility of the above-mentioned lipid peptide compound.

Specific examples of the 1,2-alkanediol include 1,2-pentanediol, 1,2-hexanediol, 1,2-octanediol, and 1,2-decanediol. Preferred examples of the 1,2-alkanediol include 1,2-pentanediol, 1,2-hexanediol, and 1,2-octanediol. 1,2-pentanediol or 1,2-hexanediol is still more preferable. The 1,2-alkanediol used in the present invention is at least one of the above-mentioned 1,2-alkanediols, and these 1,2-alkanediols may be used singly or two or more of them may be used in combination.

Furthermore, in the solid base material for skin external application or the aqueous composition of the present invention, besides the above-mentioned 1,2-alkanediol, glycerol may be preferably used as an ingredient having the function of promoting the solubility of the lipid peptide compound. Note that some commercially available products of the above-mentioned surfactants contain glycerol as a solvent, and in the case where such a commercially available product is used, glycerol to be contained as an ingredient also similarly acts to promote the solubility of the lipid peptide compound.

In the present invention, the amount of the 1,2-alkanediol or glycerol to be contained is, for example, 1% by mass to 20% by mass, preferably 1% by mass to 10% by mass, and more preferably 1% by mass to 5% by mass with respect to the total mass of an obtained solid base material for skin external application.

In the present invention, the amount of the 1,2-alkanediol or glycerol to be contained is, for example, 2% by mass to 20% by mass, preferably 2% by mass to 10% by mass with respect to the total mass of an obtained aqueous composition.

[Fatty Acid]

The solid base material for skin external application or the aqueous composition of the present invention may further comprise a fatty acid. The fatty acid used in the present invention is preferably at least one selected from the group consisting of $C_{10-20}$ saturated and unsaturated fatty acids, and salts of these fatty acids, and examples of the fatty acid include capric acid, undecanoic acid, lauric acid, tridecanoic acid, myristic acid, pentadecanoic acid, palmitic acid, margaric acid, and stearic acid. More preferred examples of the fatty acid include capric acid, lauric acid, myristic acid, palmitic acid, and stearic acid, and among these, stearic acid is the most preferable.

In the present invention, the amount of the fatty acid to be contained is, for example, 0.1% by mass to 2.0% by mass, and preferably 0.2% by mass to 1.0% by mass with respect to the total mass of an obtained solid base material for skin external application.

In the present invention, the amount of the fatty acid to be contained is, for example, 0.5% by mass to 5% by mass, preferably 0.5% by mass to 3% by mass with respect to the total mass of an obtained aqueous composition.

Note that the fatty acid used in the present invention is at least one of the above-mentioned fatty acids, and these fatty acids may be used singly or two or more of them may be used in combination.

[Oleaginous Base]

The solid base material for skin external application of the present invention may further comprise an oleaginous base. Furthermore, the aqueous composition of the present invention also may comprise an oleaginous base. Preferred examples of the oleaginous base used in the present invention include higher (polyhydric) alcohols, such as cetanol, myristyl alcohol, oleyl alcohol, lauryl alcohol, cetostearyl alcohol, stearyl alcohol, arachyl alcohol, behenyl alcohol, jojoba alcohol, chimyl alcohol, selachyl alcohol, batyl alcohol, hexyldecanol, isostearyl alcohol, 2-octyldodecanol, and dimer diols; aralkyl alcohols, such as benzyl alcohol, and derivatives thereof; isostearic acid, behenic acid, undecylenic acid, 12-hydroxystearic acid, palmitoleic acid, oleic acid, linoleic acid, linolenic acid, erucic acid, docosahexaenoic acid, eicosapentaenoic acid, isohexadecanoic acid, anteiso-henicosanoic acid, a branched long-chain fatty acid, dimer acid, and hydrogenated dimer acid; hydrocarbons, such as liquid paraffin (mineral oil), heavy liquid isoparaffin, light liquid isoparaffin, α-olefin oligomer, polyisobutene, hydrogenated polyisobutene, polybutene, squalane, squalane derived from olive, squalene, vaseline, and solid paraffin; waxes, such as candelilla wax, carnauba wax, rice wax, Japan wax, beeswax, montan wax, ozokerite, ceresin, paraffin wax, microcrystalline wax, petrolatum, Fischer-Tropsch Wax, polyethylene wax, and an ethylene-propylene copolymer; vegetable oils and fats, such as coconut oil, palm oil, palm kernel oil, safflower oil, olive oil, castor oil, avocado oil, sesame oil, tea oil, evening primrose oil, wheat germ oil, macadamia nut oil, hazelnut oil, kukui nut oil, rose hip oil, meadowfoam oil, persic oil, tea tree oil, peppermint oil, corn oil, rapeseed oil, sunflower oil, wheat germ oil, linseed oil, cottonseed oil, soybean oil, peanut oil, rice bran oil, cacao butter, shea butter, hydrogenated coconut oil, hydrogenated castor oil, jojoba oil, and hydrogenated jojoba oil; animal oils and fats, such as beef tallow, milk fat, horse fat, egg-yolk oil, mink oil, and turtle oil; animal waxes, such as spermaceti, lanolin, and orange roughy oil; lanolins, such as liquid lanolin, reduced lanolin, adsorption-purified lanolin, acetylated lanolin, acetylated liquid lanolin, hydroxylated lanolin, polyoxyethylene lanolin, lanolin fatty acids, hard lanolin fatty acids, lanolin alcohol, acetylated lanolin alcohol, and acetylated (cetyl/lanolyl) ester; sterols, such as cholesterol, dihydrocholesterol, lanosterol, dihydrolanosterol, phytosterol, and cholic acid; sapogenins; saponins; sterol esters, such as cholesteryl acetate, cholesteryl nonanoate, cholesteryl stearate, cholesteryl isostearate, cholesteryl oleate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, acyl sarcosine alkyl esters such as isopropyl N-lauroylsarcosinate, cholesteryl 12-hydroxystearate, cholesteryl macadamiate, phytosteryl macadamiate, phytosteryl isostearate, soft lanolin fatty acid cholesteryl esters, hard lanolin fatty acid cholesteryl esters, branched long-chain fatty acid cholesteryl esters, and long-chain α-hydroxy fatty acid cholesteryl esters; lipid complexes, such as a phospholipid-cholesterol complex and a phospholipid-phytosterol complex; monohydric alcohol carboxylic esters, such as octyldodecyl myristate, hexyldecyl myristate, octyldodecyl isostearate, cetyl palmitate, octyldodecyl palmitate, cetyl octanoate, hexyldecyl octanoate, isotridecyl isononanoate, isononyl isononanoate, octyl isononanoate, isotridecyl isononanoate, isodecyl neopentanoate, isotridecyl neopentanoate, isostearyl neopentanoate, octyldodecyl neodecanoate, oleyl oleate, octyldodecyl oleate, octyldodecyl ricinoleate, octyldodecyl lanolate, hexyldecyl dimethyloctanoate, octyldodecyl erucate, hydrogenated castor oil isostearate, ethyl oleate, ethyl avocadate, isopropyl myristate, isopropyl palmitate, octyl palmitate, isopropyl isostearate, isopropyl lanolate, diethyl sebacate, diisopropyl sebacate, dioctyl sebacate, diisopropyl adipate, dibutyloctyl sebacate, diisobutyl adipate, dioctyl succinate, and triethyl citrate; oxyacid esters, such as cetyl lactate, diisostearyl malate, and hydrogenated castor oil monoisostearate; polyhydric alcohol fatty acid esters, such as glyceryl trioctanoate (glyceryl tri-2-ethylhexanoate), glyceryl trioleate, glyceryl triisostearate, glyceryl diisostearate, caprylic/capric triglyceride, caprylic/capric/myristic/stearic triglyceryl, hydrogenated rosin triglyceride (hydrogenated ester gum), rosin triglyceride (ester gum), glyceryl behenate eicosanedioate, trimethylolpropane trioctanoate, trimethylolpropane triisostearate, neopentyl glycol dioctanoate, neopentyl glycol dicaprate, 2-butyl-2-ethyl-1,3-propanediol dioctanoate, propylene glycol dioleate, pentaerythrityl tetraoctanoate, hydrogenated rosin pentaerythrityl ester, ditrimethylolpropane triethylhexanoate, ditrimethylolpropane isostearate/sebacate, pentaerythrityl triethylhexanoate, dipentaerythrityl hydroxystearate/stearate/rhodinate, diglyceryl diisostearate, polyglyceryl tetraisostearate, polyglyceryl-10 nonaisostearate, polyglyceryl-8 deca(erucate/isostearate/resinate), (hexyldecanoic acid/sebacic acid) diglyceryl oligoester, glycol distearate (ethylene glycol distearate), 3-methyl-1,5-pentanediol dineopentanoate, and 2,4-diethyl-1,5-pentanediol dineopentanoate; dimer acid derivatives or dimer diol derivatives, such as diisopropyl dimer dilinoleate, diisostearyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensates, hydrogenated castor oil dimer dilinoleate, and hydroxyalkyl dimer dilinoleyl ether; fatty acid alkanolamides, such as coconut oil fatty acid monoethanolamides (cocamide MEA), coconut oil fatty acid diethanolamides (cocamide DEA), lauric acid monoethanolamide (lauramide MEA), lauric acid diethanolamide (lauramide DEA), lauric acid monoisopropanolamide (lauramide MIPA), palmitic acid monoethanolamide (palmitamide MEA), palmitic acid diethanolamide (palmitamide DEA), and coconut oil fatty acid methylethanolamides (cocamide methyl MEA); silicones, such as dimethicone (dimethylpolysiloxane), highly-polymerized dimethicone (highly-polymerized dimethylpolysiloxane), cyclomethicone (cyclic dimethylsiloxane, decamethylcyclopentasiloxane (also simply referred to as cyclopentasiloxane)), phenyl trimethicone, diphenyl dimethicone, phenyl dimethicone, stearoxypropyldimethylamine, (aminoethylaminopropyl methicone/dimethicone) copolymers, dimethiconol, dimethiconol crosspolymers, silicone resin, silicone rubber, amino-modified silicones such as aminopropyl dimethicone and amodimethicone, cation-modified silicone, polyether-modified silicone such as dimethicone copolyol, polyglycerol-modified silicone, sugar-modified silicone, carboxylic acid-modified silicone, phosphoric acid-modified silicone, sulfuric acid-modified silicone, alkyl-modified silicone, fatty acid-modified silicone, alkyl ether-modified silicone, amino acid-modified silicone, peptide-modified silicone, fluorine-modified silicone, cation-modified and polyether-modified silicone, amino-modified and polyether-modified silicone, alkyl-modified and polyether-modified silicone, and polysiloxane-oxyalkylene copolymers; and fluorine oils, such as perfluorodecane, perfluorooctane, and perfluoropolyether.

In the present invention, the amount of the oleaginous base to be contained is, for example, 1% by mass to 50% by mass, preferably 5% by mass to 50% by mass, more preferably 10% by mass to 50% by mass with respect to the total mass of an obtained solid base material for skin external application.

In the present invention, in the case where the aqueous composition contains an oleaginous base, the amount of the oleaginous base to be contained is, for example, 50% by mass to 1% by mass, preferably 30% by mass to 1% by mass with respect to the total mass of the aqueous composition.

Note that the oleaginous base used in the present invention is at least one of the above-mentioned oleaginous bases, and these oleaginous bases may be used singly or two or more of them may be used in combination.

[Organic Acid]

The solid base material for skin external application of the present invention may further comprise an organic acid. Furthermore, the aqueous composition of the present invention also may comprise an organic acid.

Examples of the organic acid include ascorbic acid, citric acid, lactic acid, glycolic acid, succinic acid, acetic acid, malic acid, tartaric acid, and fumaric acid. Among these, preferred examples of the organic acid include ascorbic acid, citric acid, and lactic acid, and more preferred examples thereof include ascorbic acid and citric acid.

In the present invention, the amount of the organic acid to be contained is, for example, 1% by mass to 20% by mass, preferably 1% by mass to 10% by mass with respect to the total mass of an obtained solid base material for skin external application.

In the present invention, in the case where the aqueous composition comprises an organic acid, the amount of the organic acid to be contained is, for example, 1% by mass to 20% by mass, preferably 1% by mass to 10% by mass with respect to the total mass of the aqueous composition.

The solid base material for skin external application of the present invention may further comprise polyethylene glycol. Furthermore, the aqueous composition of the present invention also may comprise polyethylene glycol. By containing the polyethylene glycol, the temporal stability of the solid base material for skin external application can be improved. As the above-mentioned polyethylene glycol, polyethylene glycol, for example, having an average molecular weight of 1,000 to 4,000 may be preferably used.

In the present invention, the amount of the polyethylene glycol to be contained is, for example, 1% by mass to 20% by mass, and preferably 1% by mass to 10% by mass with respect to the total mass of an obtained solid base material for skin external application.

In the present invention, in the case where the aqueous composition comprises polyethylene glycol, the amount of the polyethylene glycol to be contained is, for example, 1% by mass to 20% by mass, preferably 1% by mass to 10% by mass with respect to the total mass of the aqueous composition.

[Other Additives]

The solid base material for skin external application or the aqueous composition of the present invention may contain an additive generally usable as an additive for cosmetics and an additive for quasi drugs, as necessary. Examples of additive ingredients such as a physiologically active substance and a functional substance that are contained in skin external preparations, such as cosmetics and quasi drugs, include a moisturizer, a texture improver, a surfactant other than the above, a polymer, a thickener/gelator, a solvent, a propellant, an antioxidant, a reducing agent, an oxidizing agent, a preservative, an antimicrobial agent, an antiseptic, a chelating agent, a pH adjuster, an acid, an alkali, powder, an inorganic salt, an ultraviolet absorber, a whitening agent, vitamins and derivatives thereof, a hair growth-promoting agent, a blood circulation promoter, a stimulant, hormones, an anti-wrinkle agent, an anti-aging agent, a firming agent, a cooling agent, a warming agent, a wound-healing promoter, an abirritant, an analgesic, a cell activator, plant/animal/microbial extracts, an antipruritic, a cuticle peeling/dissolving agent, an antiperspirant, a refrigerant, a styptic, an enzyme, a nucleic acid, a perfume, a coloring agent, a colorant, a dye, a pigment, an antiphlogistic, an anti-inflammatory agent, an anti-asthmatic agent, a therapeutic agent for chronic obstructive pulmonary disease, an antiallergic agent, an immunomodulator, an anti-infective agent, and an antifungal agent.

Preferred examples of the moisturizer and the texture improver include polyols and polymers thereof, such as glycerin, 1,3-butylene glycol (1,3-butanediol), propylene glycol, 3-methyl-1,3-butanediol, 1,3-propanediol, 2-methyl-1,3-propanediol, trimethylolpropane, pentaerythritol, hexylene glycol, diglycerol, polyglycerol, diethylene glycol, polyethylene glycol, dipropylene glycol, polypropylene glycol, and an ethylene glycol-propylene glycol copolymer; glycol alkyl ethers, such as diethylene glycol monoethyl ether (ethoxydiglycol), ethylene glycol monoethyl ether, ethylene glycol monobutyl ether, and diethylene glycol dibutyl ether; water-soluble esters, such as polyglyceryl-10 (eicosanedioate/tetradecanedioate) and polyglyceryl-10 tetradecanedioate; sugar alcohols, such as sorbitol, xylitol, erythritol, mannitol, and maltitol; sugars and derivatives thereof, such as glucose, fructose, galactose, mannose, threose, xylose, arabinose, fucose, ribose, deoxyribose, maltose, trehalose, lactose, raffinose, gluconic acid, glucuronic acid, cyclodextrins (α-, β-, and γ-cyclodextrins, and modified cyclodextrins such as maltosyl cyclodextrin and hydroxyalkyl cyclodextrin), β-glucan, chitin, chitosan, heparin and derivatives thereof, pectin, arabinogalactan, dextrin, dextran, glycogen, ethyl glucoside, a glucosylethyl methacrylate polymer or copolymer; hyaluronic acid and sodium hyaluronate; sodium chondroitin sulfate; mucoitin sulfate, charonin sulfate, kerato sulfate, and dermatan sulfate; *Tremella fuciformis* extract and *Tremella fuciformis* polysaccharides; fucoidan; tuberose polysaccharides or natural polysaccharides; organic acids and salts thereof, such as citric acid, tartaric acid, and lactic acid; urea and derivatives thereof; 2-pyrrolidone-5-carboxylic acid, and salts such as a sodium salt thereof; amino acids and salts thereof, such as betaine (trimethylglycine), proline, hydroxyproline, arginine, lysine, serine, glycine, alanine, phenylalanine, tyrosine, β-alanine, threonine, glutamic acid, glutamine, asparagine, aspartic acid, cystine, cysteine, methionine, leucine, isoleucine, valine, tryptophan, histidine, and taurine; protein peptides and derivatives thereof, such as collagen, fish collagen, atelocollagen, gelatin, elastin, peptides derived from decomposed collagen, hydrolyzed collagen, hydroxypropylammonium chloride hydrolyzed collagen, peptides derived from decomposed elastin, peptides derived from decomposed keratin, hydrolyzed keratin, peptides derived from decomposed conchiolin, hydrolyzed conchiolin, peptides derived from decomposed silk protein, hydrolyzed silk, sodium lauroyl hydrolyzed silk, peptides derived from decomposed soy protein, peptides derived from decomposed wheat protein, hydrolyzed wheat protein, peptides derived from decomposed casein, and acylated peptides; acylated peptides, such as palmitoyl oligopeptide, palmitoyl pentapeptide, and palmitoyl tetrapeptide; silylated peptides; a culture medium of lactic acid bacteria, a yeast extract solution, eggshell membrane protein, bovine submaxillary mucin, hypotaurine, sesame lignan glycosides, glutathione, albumin, and whey; choline chloride and phosphorylcholine; and animal and plant extract components, such as a placenta extract solution, elastin, collagen, aloe extract, *Hammamelis virginiana* water, *Luffa cylindrica* water, *Chamomilla recutita* extract, licorice extract, comfrey extract, silk extract, *Rosa roxburghii* extract, *Achillea millefolium* extract, *Eucalyptus globulus* extract, and melilot extract, and ceramides, such as natural ceramides (types 1, 2, 3, 4, 5, and 6), hydroxyceramide, pseudoceramide, sphingoglycolipid, a ceramide-containing extract, and a glucosylceramide-containing extract.

Preferred examples of the surfactant include an anionic surfactant, a nonionic surfactant, a cationic surfactant, an amphoteric surfactant, and a polymer surfactant. The preferred surfactants are exemplified below. Preferred examples of the anionic surfactant include fatty acid salts, such as potassium laurate and potassium myristate; alkylsulfuric acid ester salts, such as sodium lauryl sulfate, triethanolamine lauryl sulfate, and ammonium lauryl sulfate; polyoxyethylene alkylsulfates, such as sodium laureth sulfate and triethanolamine laureth sulfate; acyl N-methylamino acid salts, such as sodium cocoyl methyl taurate, potassium cocoyl methyl taurate, sodium lauroyl methyl taurate, sodium myristoyl methyl taurate, sodium lauroyl methylalaninate, sodium lauroyl sarcosinate, triethanolamine lauroyl sarcosinate, and sodium lauroyl glutamate methylalaninate; acyl amino acid salts, such as sodium cocoyl glutamate, triethanolamine cocoyl glutamate, sodium lauroyl glutamate, sodium myristoyl glutamate, sodium stearoyl glutamate, ditriethanolamine palmitoyl aspartate, and triethanolamine cocoyl alaninate; polyoxyethylene alkyl ether acetates, such as sodium laureth acetate; succinic acid ester salts, such as sodium lauroyl monoethanolamide succinate; fatty acid alkanolamide ether carboxylates; acyl lactates; polyoxyethylene fatty amine sulfates; fatty acid alkanolamide sulfates; fatty acid glyceride sulfates, such as glycerin hydrogenated coconut oil fatty acid sulfate sodium salts; alkylbenzene polyoxyethylene sulfates; olefin sulfonates, such as sodium α-olefin sulfonate; alkyl sulfosuccinates, such as disodium lauryl sulfosuccinate and sodium dioctyl sulfosuccinate; alkyl ether sulfosuccinates, such as disodium laureth sulfosuccinate, sodium monolauroyl monoethanolamide polyoxyethylene sulfosuccinate, and sodium lauryl polypropylene glycol sulfosuccinate; alkylbenzene sulfonates, such as sodium tetradecylbenzene sulfonate and triethanolamine tetradecylbenzene sulfonate; alkyl naphthalene sulfonates; alkane sulfonates; α-sulfofatty acid methyl ester salts; acyl isethionates; alkyl glycidyl ether sulfonates; alkyl sulfoacetate; alkyl ether phosphates, such as sodium laureth phosphate, sodium dilaureth phosphate, sodium trilaureth phosphate, and sodium monooreth phosphate; alkyl phosphates, such as potassium lauryl phosphate; sodium caseinate; alkyl aryl ether phosphates; fatty acid amide ether phosphates; phospholipids, such as phosphatidylglycerol, phosphatidylinositol, and phosphatidic acid; and silicone anionic surfactants, such as carboxylic acid-modified silicone, phosphoric acid-modified silicone, and sulfuric acid-modified silicone. Preferred examples of the nonionic surfactant include polyoxyethylene alkyl ethers having various numbers of polyoxyethylenes, such as laureths (polyoxyethylene lauryl ethers), ceteths (polyoxyethylene cetyl ethers), steareths (polyoxyethylene stearyl ethers), behaneths (polyoxyethylene behenyl ethers), isosteareths (polyoxyethylene isostearyl ethers), and octyldodeceths (polyoxyethylene octyldodecyl ethers); polyoxyethylene alkyl phenyl ethers; castor oil derivatives and hydrogenated castor oil derivatives, such as polyoxyethylene hydrogenated castor oil, polyoxyethylene castor oil, polyoxyethylene hydrogenated castor oil monoisostearate, polyoxyethylene hydrogenated castor oil triisostearate, polyoxyethylene hydrogenated castor oil monopyroglutamate monoisostearate diester, and polyoxyethylene hydrogenated castor oil maleate; polyoxyethylene phytosterol; polyoxyethylene cholesterol; polyoxyethylene cholestanol; polyoxyethylene lanolin; polyoxyethylene reduced lanolin; polyoxyethylene-polyoxypropylene alkyl ethers, such as polyoxyethylene-polyoxypropylene cetyl ether, polyoxyethylene-polyoxypropylene 2-decyltetradecyl ether, polyoxyethylene-polyoxypropylene monobutyl ether, polyoxyethylene-polyoxypropylene hydrogenated lanolin, and polyoxyethylene-polyoxypropylene glycerin ether; polyoxyethylene-polyoxypropylene glycol; (poly) glycerin polyoxypropylene glycols, such as PPG-9 diglyceryl; glycerin fatty acid partial esters, such as glyceryl stearate, glyceryl isostearate, glyceryl palmitate, glyceryl myristate, glyceryl oleate, glyceryl cocoate, glycerin monocottonseed oil fatty acid esters, glycerin monoerucate, glycerin sesquioleate, glycerin α,α'-oleate pyroglutamate, and glycerin monostearate malate; polyglycerin fatty acid esters, such as polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, polyglyceryl-6 distearate, polyglyceryl-10 distearate, polyglyceryl-2 tristearate, polyglyceryl-10 decastearate, polyglyceryl-2 isostearate, polyglyceryl-3 isostearate, polyglyceryl-4 isostearate, polyglyceryl-5 isostearate, polyglyceryl-6 isostearate, polyglyceryl-8 isostearate, polyglyceryl-10 isostearate, polyglyceryl-2 diisostearate (diglyceryl diisostearate), polyglyceryl-3 diisostearate, polyglyceryl-10 diisostearate, polyglyceryl-2 tri isostearate, polyglyceryl-2 tetraisostearate, polyglyceryl-10 decaisostearate, polyglyceryl-2 oleate, polyglyceryl-3 oleate, polyglyceryl-4 oleate, polyglyceryl-5 oleate, polyglyceryl-6 oleate, polyglyceryl-8 oleate, polyglyceryl-10 oleate, polyglyceryl-6 dioleate, polyglyceryl-2 trioleate, and polyglyceryl-10 decaoleate; ethylene glycol mono-fatty acid esters, such as ethylene glycol monostearate; propylene glycol mono-fatty acid esters, such as propylene glycol monostearate; pentaerythritol fatty acid partial esters; sorbitol fatty acid partial esters; maltitol fatty acid partial esters; maltitol ether; sorbitan fatty acid esters, such as sorbitan monooleate, sorbitan monoisostearate, sorbitan monolaurate, sorbitan monopalmitate, sorbitan monostearate, sorbitan sesquioleate, sorbitan trioleate, sorbitan penta-2-ethylhexylate diglycerol, and sorbitan tetra-2-ethylhexylate diglycerol; sugar derivative partial esters, such as sucrose fatty acid esters, methyl glucoside fatty acid esters, and trehalose undecylenoate; alkyl glucosides, such as caprylyl glucoside; alkyl polyglycosides; lanolin alcohol; reduced lanolin; polyoxyethylene fatty acid monoesters and diesters, such as polyoxyethylene distearate, polyethylene glycol diisostearate, polyoxyethylene monooleate, and polyoxyethylene dioleate; polyoxyethylene-propylene glycol fatty acid esters; polyoxyethylene glycerin fatty acid esters, such as polyoxyethylene monooleates such as polyoxyethylene glycerin monostearate, polyoxyethylene glycerin monoisostearate, and polyoxyethylene glycerin triisostearate; polyoxyethylene sorbitan fatty acid esters, such as polyoxyethylene sorbitan monooleate, polyoxyethylene sorbitan monostearate, polyoxyethylene sorbitan monooleate, and polyoxyethylene sorbitan tetraoleate; polyoxyethylene sorbitol fatty acid esters, such as polyoxyethylene sorbitol monolaurate, polyoxyethylene sorbitol monooleate, polyoxyethylene sorbitol pentaoleate, and polyoxyethylene sorbitol monostearate; polyoxyethylene methyl glucoside fatty acid esters; polyoxyethylene alkyl ether fatty acid esters; polyoxyethylene-modified animal and vegetable fats and oils, such as polyoxyethylene sorbitol beeswax; alkyl glyceryl ethers, such as isostearyl glyceryl ether, chimyl alcohol, selachyl alcohol, and batyl alcohol; polyhydric alcohol alkyl ethers; polyoxyethylene alkylamines; tetrapolyoxyethylene/tetrapolyoxypropylene-ethylenediamine condensates; natural surfactants, such as saponin and sophorolipid; polyoxyethylene fatty acid amides; fatty acid alkanolamides, such as coconut oil fatty acid monoethanolamides (cocamide MEA), coconut oil fatty acid diethanolamides (cocamide DEA), lauric acid monoethanolamide (lauramide MEA), lauric acid diethanolamide (lauramide DEA), lauric acid monoisopropanolamide (lauramide MIPA), palmitic acid monoethanolamide (palmitamide MEA), palmitic acid diethanolamide (palmitamide DEA), and coconut oil fatty acid methylethanolamides (cocamide methyl MEA); alkyl dimethylamine oxides, such as lauramine oxide, cocamine oxide, stearamine oxide, and behenamine oxide; alkyl ethoxydimethylamine oxides; polyoxyethylene alkyl mercaptans; and silicone nonionic surfactants, such as polyether-modified silicone such as dimethicone copolyol, a polysiloxane-oxyalkylene copolymer, polyglycerol-modified silicone, and sugar-modified silicone. Preferred examples of the cationic surfactant include alkyl trimethylammonium chlorides, such as behentrimonium chloride, steartrimonium chloride, cetrimonium chloride, and lauryltrimonium chloride; alkyl trimethylammonium bromides, such as steartrimonium bromide; dialkyl dimethylammonium chlorides, such as distearyldimonium chloride and dicocodimonium chloride; fatty acid amide amines, such as stearamidopropyl dimethylamine and stearamidoethyldiethylamine, and salts thereof; alkyl ether amines, such as stearoxypropyldimethylamine, and salts or quaternary salts thereof; fatty acid amide quaternary ammonium salts, such as branched long-chain fatty acid (12 to 31) aminopropylethyldimethylammonium ethyl sulfates and lanolin fatty acid aminopropylethyldimethylammonium ethyl sulfates; polyoxyethylene alkylamines, and salts or quaternary salts thereof; alkylamine salts; fatty acid amide guanidium salts; alkyl ether ammonium salts; alkyl trialkylene glycol ammonium salts; benzalkonium salts; benzethonium salts; pyridinium salts, such as cetylpyridinium chloride; imidazolinium salts; alkyl isoquinolinium salts; dialkyl morpholinium salts; polyamine fatty acid derivatives; and silicone cationic surfactants, such as amino-modified silicone such as aminopropyl dimethicone and amodimethicone, cation-modified silicone, cation-modified and polyether-modified silicone, and amino-modified and polyether-modified silicone. Preferred examples of the amphoteric surfactant include N-alkyl-N,N-dimethylamino acid betaines, such as lauryl betaine (lauryl dimethylaminoacetic acid betaine); fatty acid amido alkyl-N,N-dimethylamino acid betaines, such as cocamide propyl betaine and lauramide propyl betaine; imidazoline betaines, such as sodium cocoamphoacetate and sodium lauroamphoacetate; alkyl sulfobetaines, such as alkyl dimethyltaurine; betaine sulfates, such as alkyl dimethylaminoethanol sulfate; betaine phosphates, such as alkyl dimethylaminoethanol phosphate; phospholipids, such as phosphatidylcholine, phosphatidylethanolamine, phosphatidylserine, sphingophospholipids such as sphingomyelin, lysolecithin, hydrogenated soybean phospholipid, partially hydrogenated soybean phospholipid, hydrogenated egg yolk phospholipid, partially hydrogenated egg yolk phospholipid, and hydroxylated lecithin; and silicone amphoteric surfactants. Preferred examples of the polymer surfactant include polyvinyl alcohol, sodium alginate, starch derivatives, tragacanth gum, and an acrylic acid-alkyl methacrylate copolymer; and various silicone surfactants.

Examples of the polymer, the thickener, and the gelator include guar gum, locust bean gum, quince seed, carrageenan, galactan, gum arabic, tara gum, tamarind, furcellaran, karaya gum, *Abelmoschus manihot*, cara gum, tragacanth gum, pectin, pectic acid and salts such as a sodium salt thereof, alginic acid and salts such as a sodium salt thereof, and mannan; starches, such as rice starch, corn starch, potato starch, and wheat starch; xanthan gum, dextran, succinoglucan, curdlan, hyaluronic acid and salts thereof, xanthan gum, pullulan, gellan gum, chitin, chitosan, agar, brown algae extract, chondroitin sulfate, casein, collagen, gelatin, and albumin; cellulose and derivatives thereof, such as methyl cellulose, ethyl cellulose, hydroxyethyl cellulose, hydroxypropyl cellulose, hydroxypropyl methylcellulose, carboxymethyl cellulose and salt such as a sodium salt thereof, methylhydroxypropyl cellulose, sodium cellulose sulfate, dialkyldimethylammonium cellulose sulfate, crystalline cellulose, and cellulose powder; starch derivatives, such as soluble starch, starch polymers such as carboxymethyl starch, methylhydroxypropyl starch, and methyl starch, starch hydroxypropyltrimonium chloride, and aluminum corn starch octenylsuccinate; alginic acid derivatives, such as sodium alginate and propylene glycol alginate; polyvinylpyrrolidone (PVP), polyvinyl alcohol (PVA), a vinylpyrrolidone-vinyl alcohol copolymer, and polyvinyl methyl ether; polyethylene glycol, polypropylene glycol, and a polyoxyethylene-polyoxypropylene copolymer; amphoteric methacrylic ester copolymers, such as a (methacryloyloxyethylcarboxybetaine/alkyl methacrylate) copolymer and an (acrylate/stearyl acrylate/ethylamine oxide methacrylate) copolymer; a (dimethicone/vinyl dimethicone) crosspolymer, an (alkyl acrylate/diacetone acrylamide) copolymer, and an (alkyl acrylate/diacetone acrylamide) copolymer AMP; a partially saponified polyvinyl acetate, maleic acid copolymer; a vinylpyrrolidone-dialkylaminoalkyl methacrylate copolymer; an acrylic resin alkanolamine; polyester, and water-dispersible polyester; polyacrylamide; a copolymer of a polyacrylic ester such as polyethyl acrylate, a carboxy vinyl polymer, polyacrylic acid and salts such as a sodium salt thereof, an acrylic acid-methacrylic acid ester copolymer; an acrylic acid-alkyl methacrylate copolymer; cationized cellulose such as polyquaternium-10, a diallyldimethylammonium chloride-acrylamide copolymer such as polyquaternium-7, an acrylic acid-diallyldimethylammonium chloride copolymer such as polyquaternium-22, an acrylic acid-diallyldimethylimonium chloride-acrylamide copolymer such as polyquaternium-39, an acrylic acid-cationized methacrylic ester copolymer, an acrylic acid-cationized methacrylic amide copolymer, an acrylic acid-methyl acrylate-methacrylamidopropyltrimethylammonium chloride copolymer such as polyquaternium-47, and a methacryloyl chloride choline ester polymer; cationized polysaccharides, such as a cationized oligosaccharide, cationized dextran, and guar hydroxypropyltrimonium chloride; polyethyleneimine; a cationic polymer; a copolymer of 2-methacryloyloxyethyl phosphorylcholine and butyl methacrylate such as polyquaternium-51; polymer emulsions, such as an acrylic resin emulsion, a poly(ethyl acrylate) emulsion, a polyacrylalkyl ester emulsion, a polyvinyl acetate resin emulsion, a natural rubber latex, and a synthetic latex; nitrocellulose; polyurethanes and various copolymers thereof; various silicones; various silicone copolymers, such as an acrylic-silicone graft copolymer; various fluorine polymers; 12-hydroxystearic acid and salts thereof; dextrin fatty acid esters, such as dextrin palmitate and dextrin myristate; silicic anhydride, fumed silica (silicic anhydride ultrafine particles), magnesium aluminum silicate, magnesium sodium silicate, a metallic soap, a metal dialkyl phosphate, bentonite, hectorite, organo-modified clay mineral, a sucrose fatty acid ester, and a fructooligosaccharide fatty acid ester. Among these examples, cellulose and derivatives thereof, alginic acid and salts thereof, polyvinyl alcohol, hyaluronic acid and salts thereof, or collagen is more preferable.

Preferred examples of the solvents and the propellants include lower alcohols, such as ethanol, 2-propanol (isopropyl alcohol), butanols, and isobutyl alcohol; glycols, such as propylene glycol, 1,3-butylene glycol, diethylene glycol, dipropylene glycol, and isopentyldiol; glycol ethers, such as diethylene glycol monoethyl ether (ethoxy diglycol), ethylene glycol monoethyl ether, ethylene glycol monobutyl ether, triethylene glycol monoethyl ether, diethylene glycol diethyl ether, diethylene glycol dibutyl ether, propylene glycol monoethyl ether, and dipropylene glycol monoethyl ether; glycol ether esters, such as ethylene glycol monoethyl ether acetate, diethylene glycol monoethyl ether acetate, and propylene glycol monoethyl ether acetate; glycol esters, such as diethoxyethyl succinate and ethylene glycol disuccinate; benzyl alcohol, benzyloxyethanol, propylene carbonate, dialkyl carbonate, acetone, ethyl acetate, and N-methylpyrrolidone; toluene; fluorocarbon, and next-generation fluorocarbon; and propellants such as LPG, dimethyl ether, and carbon dioxide gas.

Preferred examples of the antioxidant include tocopherol (vitamin E), and tocopherol derivatives such as tocopherol acetate; BHT, and BHA; gallic acid derivatives, such as propyl gallate; vitamin C (ascorbic acid) and/or derivatives thereof; erythorbic acid and derivatives thereof; sulfites, such as sodium sulfite; hydrogen sulfites, such as sodium hydrogen sulfite; thiosulfates, such as sodium thiosulfate; hydrogen metasulfites; thiotaurine, and hypotaurine; and thioglycerol, thiourea, thioglycolic acid, and cysteine hydrochloride.

Preferred examples of the reducing agent include thioglycolic acid, cysteine, and cysteamine.

Preferred examples of the oxidizing agent include an hydrogen peroxide solution, ammonium persulfate, sodium bromate, and percarbonic acid.

Preferred examples of the preservative, the antimicrobial agent, and the antiseptic include hydroxybenzoic acids, such as methylparaben, ethylparaben, propylparaben, and butylparaben, and salts or esters thereof; salicylic acid; sodium benzoate; phenoxyethanol; isothiazolinone derivatives, such as methylchloroisothiazolinone and methylisothiazolinone; imidazolinium urea; dehydroacetic acid and salts thereof; phenols; halogenated bisphenols such as triclosan, acid amides thereof, and quaternary ammonium salts thereof; trichlorocarbanide, zinc pyrithione, benzalkonium chloride, benzethonium chloride, sorbic acid, chlorhexidine, chlorhexidine gluconate, halocarban, hexachlorophene, and hinokitiol; other phenols, such as phenol, isopropylphenol, cresol, thymol, parachlorophenol, phenylphenol, and sodium phenylphenate; and phenylethyl alcohol, photosensitizing dyes, antimicrobial zeolite, and a silver ion.

Preferred examples of the chelating agent include edetates (ethylenediamine tetraacetates), such as EDTA, EDTA-2Na, EDTA-3Na, and EDTA-4Na; hydroxyethylethylenediamine triacetates, such as HEDTA-3Na; pentetates (diethylenetriamine pentaacetate); phytic acid; phosphonic acids such as etidronic acid, and salts such as a sodium salt thereof; polyamino acids, such as polyaspartic acid and polyglutamic acid; sodium polyphosphate, sodium metaphosphate, and phosphoric acid; and sodium citrate, citric acid, alanine, dihydroxyethylglycine, gluconic acid, ascorbic acid, succinic acid, and tartaric acid.

Preferred examples of the pH adjuster, the acid, and the alkali include citric acid, sodium citrate, lactic acid, sodium lactate, potassium lactate, glycolic acid, succinic acid, acetic acid, sodium acetate, malic acid, tartaric acid, fumaric acid, phosphoric acid, hydrochloric acid, sulfuric acid, monoethanolamine, diethanolamine, triethanolamine, isopropanolamine, triisopropanolamine, 2-amino-2-methyl-1,3-propanediol, 2-amino-2-hydroxymethyl-1,3-propanediol, arginine, sodium hydroxide, potassium hydroxide, aqueous ammonia, guanidine carbonate, and ammonium carbonate.

Preferred examples of the powder include inorganic powder having various sizes and shapes, such as mica, talc, kaolin, sericite, montmorillonite, kaolinite, mica, muscovite, phlogopite, synthetic mica, lepidolite, biotite, vermiculite, magnesium carbonate, calcium carbonate, aluminum silicate, barium silicate, calcium silicate, magnesium silicate, strontium silicate, metal tungstates, magnesium, zeolite, barium sulfate, calcined calcium sulfate, calcium phosphate, fluorapatite, hydroxyapatite, ceramic powder, bentonite, smectite, clay, mud, metallic soaps (for example, zinc myristate, calcium palmitate, and aluminum stearate), calcium carbonate, red iron oxide, yellow iron oxide, black iron oxide, ultramarine, prussian blue, carbon black, titanium oxide, titanium oxide fine particles and titanium oxide ultrafine particles, zinc oxide, zinc oxide fine particles and zinc oxide ultrafine particles, alumina, silica, fumed silica (silicic anhydride ultrafine particles), titanated mica, fish scale, boron nitride, photochromic pigments, synthetic fluorophlogopite, particulate composite powder, gold, and aluminum, and inorganic powder, such as hydrophobic or hydrophilic powder, obtained by treatment of the above mentioned powder with various surface treating agents such as silicones, such as hydrogen silicone and cyclic hydrogen silicone, other silanes, or titanium coupling agents; and organic powder, surface-treated powder, and organic-inorganic composite powder, each having various sizes and shapes, such as starch, cellulose, nylon powder, polyethylene powder, polymethyl methacrylate powder, polystyrene powder, styrene-acrylic acid copolymer resin powder, polyester powder, benzoguanamine resin powder, polyethylene terephthalate-polymethyl methacrylate laminated powder, polyethylene terephthalate-aluminum-epoxy laminated powder, urethane powder, silicone powder, and Teflon (registered trademark) powder.

Preferred examples of the inorganic salts include sodium chloride-containing salts, such as common salt, regular salt, rock salt, sea salt, and natural salt; potassium chloride, aluminum chloride, calcium chloride, magnesium chloride, bittern, zinc chloride, and ammonium chloride; sodium sulfate, aluminum sulfate, aluminum potassium sulfate (alum), aluminum ammonium sulfate, barium sulfate, calcium sulfate, potassium sulfate, magnesium sulfate, zinc sulfate, iron sulfate, and copper sulfate; and sodium phosphates such as mono-, di-, and tri-sodium phosphates, potassium phosphates, calcium phosphates, and magnesium phosphates.

Preferred examples of the ultraviolet absorber include benzoate ultraviolet absorbers, such as p-aminobenzoic acid, p-aminobenzoic acid monoglycerin ester, N,N-dipropoxy-p-aminobenzoic acid ethyl ester, N,N-diethoxy-p-aminobenzoic acid ethyl ester, N,N-dimethyl-p-aminobenzoic acid ethyl ester, N,N-dimethyl-p-aminobenzoic acid butyl ester, and N,N-dimethyl-p-aminobenzoic acid ethyl ester; anthranilate ultraviolet absorbers, such as homomethyl-N-acetylanthranilate; salicylate ultraviolet absorbers, such as salicylic acid and a sodium salt thereof, amyl salicylate, menthyl salicylate, homomenthyl salicylate, octyl salicylate, phenyl salicylate, benzyl salicylate, and p-isopropanolphenyl salicylate; cinnamate ultraviolet absorbers, such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, 2-ethylhexyl p-methoxycinnamate (octyl p-methoxycinnamate), 2-ethoxyethyl p-methoxycinnamate (cinoxate), cyclohexyl p-methoxycinnamate, ethyl α-cyano-β-phenylcinnamate, 2-ethylhexyl α-cyano-β-phenylcinnamate (octocrylene), glyceryl mono-2-ethylhexanoyl di-p-methoxycinnamate, ferulic acid, and derivatives thereof; benzophenone ultraviolet absorbers, such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone (oxybenzone-3), 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octoxybenzophenone, and 4-hydroxy-3-carboxybenzophenone; 3-(4'-methylbenzylidene)-d,l-camphor, and 3-benzylidene-d,l-camphor; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenylbenzotriazole; dibenzalazine; dianisoyltmethane; 5-(3,3-dimethyl-2-norbornylidene)-3-pentan-2-one; dibenzoylmethane derivatives, such as 4-t-butylmethoxydibenzoylmethane; octyl triazone; urocanic acid, and urocanic acid derivatives such as ethyl urocanate; and 2-(2'-hydroxy-5'-methylphenyl)benzotriazole, 1-(3,4-dimethoxyphenyl)-4,4-dimethyl-1,3-pentanedione, hydantoin derivatives such as 2-ethylhexyl dimethoxybenzylidene dioxoimidazolidine propionate, phenylbenzimidazole sulfonic acid, terephthalylidene dicamphor sulfonic acid, drometrizole trisiloxane, methyl anthranilate, rutin and derivatives thereof, and oryzanol and derivatives thereof.

Preferred examples of the whitening agent include hydroquinone glycosides such as arbutin and α-arbutin, and esters thereof; ascorbic acid, and ascorbic acid derivatives, such as ascorbyl phosphates such as sodium ascorbyl phosphate and magnesium ascorbyl phosphate, ascorbyl fatty acid esters such as ascorbyl tetraisopalmitate, ascorbic acid alkyl ethers such as ascorbic acid ethyl ether, ascorbic acid glucoside such as ascorbic acid 2-glucoside and fatty acid esters thereof, ascorbyl sulfate, and tocopheryl ascorbyl phosphate; and kojic acid, ellagic acid, tranexamic acid and derivatives thereof, ferulic acid and derivatives thereof, placenta extract, glutathione, oryzanol, butylresorcinol, and plant extracts such as oil-soluble *Chamomilla recutita* extract, oil-soluble licorice extract, *Tamarix chinensis* extract, and saxifrage extract.

Preferred examples of the vitamins and derivatives thereof include vitamin A, such as retinol, retinol acetate, and retinol palmitate; vitamin Bs, such as thiamine hydrochloride, thiamine sulfate, riboflavin, riboflavin acetate, pyridoxine hydrochloride, pyridoxine dioctanoate, pyridoxine dipalmitate, flavin adenine dinucleotide, cyanocobalamin, folic acids, nicotinic acids such as nicotinamide and benzyl nicotinate, and cholines; vitamin C, such as ascorbic acid and salts such as a sodium salt thereof; vitamin D; vitamin E, such as α-, β-, γ-, and δ-tocopherols; other vitamins, such as pantothenic acid and biotin; ascorbic acid derivatives, such as ascorbyl phosphates such as sodium ascorbyl phosphate and magnesium ascorbyl phosphate, ascorbyl fatty acid esters such as ascorbyl tetraisopalmitate, ascorbyl stearate, ascorbyl palmitate, and ascorbyl dipalmitate, ascorbic acid alkyl ethers such as ascorbic acid ethyl ether, ascorbic acid glucosides such as ascorbic acid 2-glucoside and fatty acid esters thereof, and tocopheryl ascorbyl phosphate; vitamin derivatives, such as tocopherol derivatives such as tocopherol nicotinate, tocopherol acetate, tocopherol linoleate, tocopherol ferulate, and tocopherol phosphate, tocotrienol, and other various vitamin derivatives.

Preferred examples of the hair growth-promoting agent, the blood circulation-promoter, and the stimulant include plant extracts and tinctures, such as swertia herb extract, *capsicum* tincture, ginger tincture, ginger extract, and cantharis tincture; and capsaicin, nonylic acid vanillylamide, zingerone, ichthammol, tannic acid, borneol, cyclandelate, cinnarizine, tolazoline, acetylcholine, verapamil, cepharanthine, γ-oryzanol, vitamin E and derivatives thereof such as tocopherol nicotinate and tocopherol acetate, γ-oryzanol, nicotinic acid and derivatives thereof such as nicotinamide, benzyl nicotinate, inositol hexanicotinate, and nicotinic alcohol, allantoin, Photosensitizing dye 301, Photosensitizing dye 401, carpronium chloride, pentadecanoic acid monoglyceride, flavanonol derivatives, stigmasterol and stigmastanol and glycosides thereof, and minoxidil.

Preferred examples of the hormones include estradiol, estrone, ethynylestradiol, cortisone, hydrocortisone, and prednisone. Preferred examples of other therapeutic agents such as the anti-wrinkle agent, the anti-aging agent, the firming agent, the cooling agent, the warming agent, the wound-healing promoter, the abirritant, the analgesic, and the cell activator include retinols, retinoic acids, and tocopheryl retinoate; lactic acid, glycolic acid, gluconic acid, fruit acid, salicylic acid, and derivatives such as glycosides and esters thereof, and α- or β-hydroxy acids and derivatives thereof, such as hydroxycapric acid, long-chain α-hydroxy fatty acids, and long-chain α-hydroxy fatty acid cholesteryl esters; γ-aminobutyric acid, and γ-amino-β-hydroxybutyric acid; carnitine; carnosine; creatine; ceramides, and sphingosines; caffeine, xanthine, and derivatives thereof; anti-oxidizing agents and active oxygen scavengers, such as coenzyme Q10, carotene, lycopene, astaxanthin, lutein, α-lipoic acid, colloidal platinum nanoparticles, and fullerenes; catechins; flavones, such as quercetin; isoflavones; gallic acid and sugar ester derivatives thereof; polyphenols, such as tannin, sesamin, proanthocyanidin, chlorogenic acid, and apple polyphenols; rutin and derivatives such as glycosides thereof; hesperidin and derivatives such as glycosides thereof; lignan glycosides; licorice extract related substances, such as glabridin, glabrene, liquiritin, and isoliquiritin; lactoferrin; shogaol, and gingerol; perfume substances, such as menthol and cedrol, and derivatives thereof; capsaicin and vanillin, and derivative thereof; insect repellents, such as diethyltoluamide; and complexes of a physiologically active substance and cyclodextrins.

Preferred examples of the plant, animal, and microbial extracts include extracts, such as iris extract, *Angelica keiskei* extract, *Thujopsis dolabrata* extract, asparagus extract, avocado extract, *Hydrangea serrata* extract, almond extract, *Althaea officinalis* extract, *Arnica montana* extract, aloe extract, apricot extract, apricot kernel extract, ginkgo extract, *Artemisia capillaris* flower extract, fennel seed extract, turmeric root extract, oolong tea extract, *uva-ursi* extract, rose fruit extract, *Echinacea angustifolia* leaf extract, *Isodonis japonicus* extract, scutellaria root extract, *phellodendron* bark extract, coptis rhizome extract, barley extract, *Panax ginseng* extract, *hypericum* extract, *Lamium album* extract, *Ononis spinosa* extract, Nasturtium *officinale* extract, orange extract, dried sea water residues, seaweed extract, Japanese persimmon leaf extract, *Pyracantha fortuneana* extract, hydrolyzed elastin, hydrolyzed wheat powder, hydrolyzed silk, *pueraria* root extract, *Chamomilla recutita* extract, oil-soluble *Chamomilla recutita* extract, carrot extract, *Artemisia capillaris* extract, *Avena fatua* extract, *Hibiscus sabdariffa* extract, licorice extract, oil-soluble licorice extract, kiwi fruit extract, kiou extract, jew's-ear extract, cinchona extract, cucumber extract, *Paulownia tomentosa* leaf extract, guanosine, guava extract, *sophora* root extract, *Gardenia jasminoides* extract, *Sasa veitchii* extract, *Sophora flavescens* extract, walnut extract, chestnut extract, grapefruit extract, *Clematis vitalba* extract, black rice extract, black sugar extract, black vinegar, *chlorella* extract, mulberry extract, gentian extract, geranium herb extract, black tea extract, yeast extract, *magnolia* bark extract, coffee extract, burdock root extract, rice extract, fermented rice extract, fermented rice bran extract, rice germ oil, comfrey extract, collagen, bilberry extract, asiasarum root extract, bupleurum root extract, umbilical cord extract solution, saffron extract, *salvia* extract, *Saponaria officinalis* extract, bamboo grass extract, *Crataegus cuneata* extract, *Bombyx mori excrementum* extract, *zanthoxylum* fruit extract, shiitake mushroom extract, rehmannia root extract, *lithospermum* root extract, *Perilla frutescens* extract, *Tilia japonica* extract, *Filipendula multijuga* extract, jatoba extract, peony root extract, ginger extract, Acorus calamus root extract, *Betula alba* extract, *Tremella fuciformis* extract, *Equisetum arvense* extract, stevia extract, stevia fermentation product, *Tamarix chinensis* extract, *Hedera helix* extract, *Crataegus oxycantha* extract, *Sambucus nigra* extract, *Achillea millefolium* extract, *Mentha piperita* extract, sage extract, mallow extract, cnidium rhizome extract, swertia herb extract, mulberry bark extract, rhubarb extract, soybean extract, jujubi extract, thyme extract, dandelion extract, lichens extract, tea extract, clove extract, *Imperata cylindrica* extract, *citrus unshiu* peel extract, tea tree oil, *Rubus suavissimus* extract, *capsicum* extract, Japanese *angelica* root extract, *Calendula officinalis* extract, peach kernel extract, bitter orange peel extract, *Houttuynia cordata* extract, tomato extract, natto extract, carrot extract, garlic extract, *Rosa multiflora* extract, *hibiscus* extract, *ophiopogon tuber* extract, lotus extract, parsley extract, birch extract, honey, *Hamamelis virginiana* extract, *Parietaria officinalis* extract, *Rabdosia japonica* extract, bisabolol, Japanese cypress extract, *Bifidobacterium* extract, loquat extract, coltsfoot extract, Japanese butterbur flower-bud extract, hoelen extract, *Ruscus aculeatus* extract, grape extract, grape seed extract, propolis, *Luffa cylindrica* extract, safflower extract, peppermint extract, *Tilia miqueliaria* extract, *Paeonia suffruticosa* extract, hop extract, *Rosa rugosa* extract, pine extract, *Aesculus hippocastanum* extract, *Lysichiton camtschatcense* extract, *Sapindus mukurossi* extract, *Melissa officinalis* extract, *Nemacystus decipiens* extract, peach extract, cornflower extract, *Eucalyptus globulus* extract, saxifrage extract, *Citrus junos* extract, lily extract, coix seed extract, *Artemisia princeps* extract, lavender extract, green tea extract, egg shell membrane extract, apple extract, rooibos tea extract, *Litchi chinensis* extract, lettuce extract, lemon extract, forsythia fruit extract, *Astragalus sinicus* extract, rose extract, rosemary extract, *Anthemis nobilis* extract, royal jelly extract, and burnt extract.

Examples of the antipruritic include diphenhydramine hydrochloride, chlorpheniramine maleate, camphor, and a substance P inhibitor.

Examples of the cuticle peeling and dissolving agent include salicylic acid, sulfur, resorcin, selenium sulfide, and pyridoxine.

Examples of the antiperspirant include aluminum chlorohydrate, aluminum chloride, zinc oxide, and zinc p-phenolsulfonate.

Examples of the refrigerant include menthol and methyl salicylate.

Examples of the styptic include citric acid, tartaric acid, lactic acid, aluminum potassium sulfate, and tannic acid.

Examples of the enzymes include superoxide dismutase, catalase, lysozyme chloride, lipase, papain, pancreatin, and protease.

Preferred examples of the nucleic acids include ribonucleic acids and salts thereof, deoxyribonucleic acids and salts thereof, and adenosine triphosphate disodium.

Preferred examples of the perfume include synthetic perfumes and natural perfumes, such as acetyl cedrene, amylcinnamaldehyde, allylamyl glycolate, β-ionone, Iso E Super, isobutylquinoline, iris oil, irone, indole, ylang-ylang oil, undecanal, undecenal, γ-undecalactone, estragole, eugenol, oakmoss, opoponax resinoid, orange oil, eugenol, aurantiol, galaxolide, carvacrol, L-carvone, camphor, canon, carrot seed oil, clove oil, methyl cinnamate, geraniol, geranyl nitrile, isobornyl acetate, geranyl acetate, dimethylbenzylcarbinyl acetate, styralyl acetate, cedryl acetate, terpinyl acetate, p-t-butylcyclohexyl acetate, vetiveryl acetate, benzyl acetate, linalyl acetate, isopentyl salicylate, benzyl salicylate, sandalwood oil, santalol, cyclamen aldehyde, cyclopentadecanolide, methyl dihydrojasmonate, dihydromyrcenol, jasmine absolute, jasmine lactone, cis-jasmone, citral, citronellol, citronellal, cinnamon bark oil, 1,8-cineole, cinnamaldehyde, *styrax* resinoid, cedarwood oil, cedrene, cedrol, celery seed oil, thyme oil, damascone, damascenone, thymol, tuberose absolute, decanal, decalactone, terpineol, γ-terpinen, triplal, nerol, nonanal, 2,6-nonadienal, nonalactone, patchouli alcohol, vanilla absolute, vanillin, basil oil, patchouli oil, hydroxycitronellal, α-pinene, piperitone, phenethyl alcohol, phenylacetaldehyde, petitgrain oil, hexylcinnamaldehyde, cis-3-hexenol, Peru balsam, vetiver oil, vetiverol, peppermint oil, pepper oil, heliotropin, bergamot oil, benzyl benzoate, borneol, mil resinoid, musk ketone, methylnonylacetaldehyde, γ-methylionone, menthol, L-menthol, L-menthone, *Eucalyptus globulus* oil, β-ionone, lime oil, lavender oil, D-limonene, linalool, lyral, lilial, lemon oil, rose absolute, rose oxide, rose oil, rosemary oil, and various essential oils, and various perfume blends of the synthetic perfumes and the natural perfumes.

Preferred examples of the coloring agent, the colorant, the dye, and the pigment include legal colors, such as Brown No. 201, Black No. 401, Violet No. 201, Violet No. 401, Blue No. 1, Blue No. 2, Blue No. 201, Blue No. 202, Blue No. 203, Blue No. 204, Blue No. 205, Blue No. 403, Blue No. 404, Green No. 201, Green No. 202, Green. No. 204, Green No. 205, Green No. 3, Green No. 401, Green No. 402, Red No. 102, Red No. 104-1, Red No. 105-1, Red No. 106, Red No. 2, Red No. 201, Red No. 202, Red No. 203, Red No. 204, Red No. 205, Red No. 206, Red No. 207, Red No. 208, Red No. 213, Red No. 214, Red No. 215, Red No. 218, Red No. 219, Red No. 220, Red No. 221, Red No. 223, Red No. 225, Red No. 226, Red No. 227, Red No. 228, Red No. 230-1, Red No. 230-2, Red No. 231, Red No. 232, Red No. 3, Red No. 401, Red No. 404, Red No. 405, Red No. 501, Red No. 502, Red No. 503, Red No. 504, Red No. 505, Red No. 506, Orange No. 201, Orange No. 203, Orange No. 204, Orange No. 205, Orange No. 206, Orange No. 207, Orange No. 401, Orange No. 402, Orange No. 403, Yellow No. 201, Yellow No. 202-1, Yellow No. 202-2, Yellow No. 203, Yellow No. 204, Yellow No. 205, Yellow No. 4, Yellow No. 401, Yellow No. 402, Yellow No. 403-1, Yellow No. 404, Yellow No. 405, Yellow No. 406, Yellow No. 407, and Yellow No. 5; other acid dyes, such as Acid Red 14; basic dyes, such as Arianor Sienna Brown, Arianor Madder Red, Arianor Steel Blue, and Arianor Straw Yellow; nitro dyes, such as HC Yellow 2, HC Yellow 5, HC Red 3,4-hydroxypropylamino-3-nitrophenol, N,N'-bis(2-hydroxyethyl)-2-nitro-p-phenylenediamine, HC Blue 2, and Basic Blue 26; disperse dyes; inorganic white pigments, such as titanium dioxide and zinc oxide; inorganic red pigments, such as iron oxide (red iron oxide) and iron titanate; inorganic brown pigments, such as γ-iron oxide; inorganic yellow pigments, such as yellow iron oxide and ocher; inorganic black pigments, such as black iron oxide and low-order titanium oxide; inorganic violet pigments, such as mango violet and cobalt violet; inorganic green pigments, such as chromium oxide, chromium hydroxide, and cobalt titanate; inorganic blue pigments, such as ultramarine and prussian blue; pearl pigments, such as titanium oxide-coated mica, titanium oxide-coated bismuth oxychloride, titanium oxide-coated talc, colored titanium oxide-coated mica, bismuth oxychloride, and fish scale; metal powder pigments, such as aluminum powder, copper powder, and gold; surface treated inorganic and metal powder pigments; organic pigments, such as zirconium lake, barium lake, and aluminum lake; surface treated organic pigments; natural coloring agents and dyes, such as anthraquinones such as astaxanthin and alizarin, naphthoquinones such as anthocyanidin, β-carotene, catenal, capsanthin, chalcone, carthamin, quercetin, crocin, chlorophyll, curcumin, cochineal, and shikonin, bixin, flavones, betacyanidine, henna, hemoglobin, lycopene, riboflavin, and rutin; oxidation dye intermediates and couplers, such as p-phenylenediamine, toluene-2,5-diamine, o-, m-, and p-aminophenols, m-phenylenediamine, 5-amino-2-methylphenol, resorcin, 1-naphthol, and 2,6-diaminopyridine, and salts thereof; autoxidizable dyes, such as indoline; and dihydroxyacetone.

Preferred examples of the antiphlogistics and the anti-inflammatory agent include glycyrrhizic acid and derivatives thereof, glycyrrhetic acid derivatives, salicylic acid derivatives, hinokitiol, guaiazulene, allantoin, indomethacin, ketoprofen, ibuprofen, diclofenac, loxoprofen, celecoxib, infliximab, etanercept, zinc oxide, hydrocortisone acetate, prednisone, diphenhydramine hydrochloride, and chlorpheniramine maleate; and plant extracts, such as peach leaf extract and *Artemisia princeps* leaf extract.

Preferred examples of the anti-asthmatic agent, the therapeutic agent for chronic obstructive pulmonary disease, the antiallergic agent, and the immunomodulator include aminophylline, theophyllines, steroids (such as fluticasone and beclomethasone), leukotriene antagonists, thromboxane inhibitors, Intal, β2 agonists (such as formoterol, salmeterol, albuterol, tulobuterol, clenbuterol, and epinephrine), tiotropium, ipratropium, dextromethorphan, dimemorfan, bromhexine, tranilast, ketotifen, azelastine, cetirizine, chlorpheniramine, mequitazine, tacrolimus, ciclosporin, sirolimus, methotrexate, cytokine modulators, interferon, omalizumab, and proteins/antibody pharmaceuticals.

Preferred examples of the anti-infective agent and the antifungal agent include oseltamivir, zanamivir, and itraconazole. In addition to these ingredients, the solid base material for skin external application and the aqueous composition of the present invention may contain known cosmetic ingredients, known pharmaceutical ingredients, and known food ingredients, such as ingredients described in Japanese Standards of Cosmetic Ingredients, Japanese Cosmetic Ingredients Codex, List of Cosmetics Ingredients Japanese Labelling Names, issued by Japan Cosmetic Industry Association, INCI dictionary (The International Cosmetic Ingredient Dictionary and Handbook), Japanese Standards of Quasi-drag Ingredients, Japanese Pharmacopoeia, Japanese Pharmaceutical Excipients, Japan's Specifications and Standards for Food Additives, and other standards, and ingredients described in Japanese and foreign patent publications and patent application publications (including Japanese Translations of PCT International Application Publications and Re-Publications of PCT International Publications) categorized as International Patent Classification IPC of A61K7 and A61K8, in a known combination and in a known ratio and amount.

[Method for Producing the Solid Base Material for Skin External Application (1)]

The solid base material for skin external application of the present invention may be produced in such a manner that a lipid peptide compound including at least one of compounds of the above-mentioned Formulae (1) to (3) or pharmaceutically usable salts thereof is mixed with a surfactant and water, and furthermore, if desired, with a 1,2-alkanediol or glycerol, a fatty acid, an oleaginous base, an organic acid, and other additives, and stirred while being heated, and then, the mixture is left standing to cool. Furthermore, through this production process, the aqueous composition of the present invention may be produced as mentioned later.

For example, the solid base material for skin external application of the present invention is produced by the following steps of:

a) mixing the above-mentioned lipid peptide compound, a surfactant, and water, and heating the mixture to prepare a solution or a dispersion liquid, b) adding the solution or the dispersion liquid to water, and heating the mixture at room temperature or higher and lower than 100° C., and c) while stirring, cooling the mixture to a temperature lower than the temperature at the heating step, and then leaving the mixture standing to cool to form a gel solid (a solid base material for skin external application).

Note that a 1,2-alkanediol or glycerol, and a fatty acid, an oleaginous base, an organic acid, polyethylene glycol, and other additives may be added at the step of preparing the solution or the dispersion liquid in the step a), or may be added in advance to water to which the solution or the dispersion liquid is added in the step b).

The amount of water is preferably 60% by mass or more and less than 95% by mass with respect to the total mass of the obtained solid base material for skin external application.

The amount of water is preferably 50% by mass or more and less than 80% by mass with respect to the total mass of the obtained solution or dispersion liquid.

The heating temperatures in the step a) and the step b) each are preferably 50° C. to 90° C., more preferably 60° C. to 90° C., for example, 80° C., and the stirring of the respective mixtures are preferably performed while the heating thereof. Here, the heating and stirring time in each of the steps depends on the lipid peptide compounds, the surfactants, and other ingredients to be used, and depends on the amounts of these ingredients to be contained, but, typically, these ingredients are capable of being dissolved or dispersed within about 5 minutes to 50 minutes.

Subsequent to the steps a) and b), the mixture is cooled while being stirred until the temperature of a liquid reaches a temperature lower than the temperature in the step b) (the step c)). Here, the cooling temperature is, for example, room temperature to about 80° C., room temperature to about 60° C., or room temperature to about 40° C.

[Method for Producing the Aqueous Composition and the Solid Base Material for Skin External Application (2)]

A method for producing the solid base material for skin external application by using the aqueous composition of the present invention will be described below.

As described in detail below, the aqueous composition is produced through the step a) of the above-mentioned [Method for producing the solid base material for skin external application (1)].

<Method for Producing the Aqueous Composition>

To produce the aqueous composition, first, a lipid peptide compound including at least one of compounds of the above-mentioned Formulae (1) to (3) or pharmaceutically usable salts thereof is mixed with a surfactant and water, and heated to prepare a solution or a dispersion liquid. During the preparation of the solution or the dispersion liquid, if desired, a 1,2-alkanediol or glycerol, and/or a fatty acid may be added, and furthermore, an oleaginous base, an organic acid, polyethylene glycol, and other additives may be added.

Then, this solution or this dispersion liquid is cooled, whereby the aqueous composition can be obtained.

The heating temperature is preferably 50° C. to 90° C., more preferably 60° C. to 90° C., for example, 80° C. During the heating, stirring is preferably performed. The heating (stirring) time depends on the lipid peptide compounds, the surfactants, and other ingredients to be used, and depends on the amounts of these ingredients to be contained, but, typically, the heating (stirring) time is about 5 minutes to 50 minutes, whereby a solution or a dispersion liquid in which the ingredients contained are dissolved or dispersed is obtained.

More preferably, while being stirred, the obtained solution or dispersion liquid is preferably cooled to a temperature lower than the heating temperature, for example, room temperature to about 80° C., room temperature to about 60° C., or room temperature to about 40° C., and then, the stirring of the solution or dispersion liquid is stopped, and the solution or dispersion liquid is left standing.

The amount of water is preferably 50% by mass or more and less than 80% by mass with respect to the total mass of the obtained aqueous composition.

The aqueous composition thus obtained is useful as a premix for the preparation of the solid base material for skin external application, and the solid base material for skin external application can be easily prepared by adding water and other active ingredients to the composition as described later.

<Method for Producing the Solid Base Material for Skin External Application by Using the Aqueous Composition>

Using the aqueous composition of the present invention, the solid base material for skin external application can be produced, for example, through the following steps 1) to 3):

1) heating the aqueous composition at room temperature or higher and less than 100° C.;

2) adding the heated aqueous composition to an aqueous phase heated at room temperature or higher and less than 100° C., followed by mixing; and 3) cooling the obtained mixture to form a gel.

The aqueous phase comprises water, and may further comprise an oleaginous base, and furthermore, may comprise a 1,2-alkanediol or glycerol, a fatty acid, an organic acid, polyethylene glycol, and other additives.

In the case where an organic acid is added to the solid base material for skin external application, an organic acid-containing solid base material for skin external application can be produced, for example, through the following steps 4) to 7):

4) heating the aqueous composition at room temperature or higher and less than 100° C.;

5) adding the heated aqueous composition to an aqueous phase heated at room temperature or higher and less than 100° C., followed by mixing;

6) cooling the obtained mixture to form a gel; and 7) adding a mixed solution of water and an organic acid to the mixture during the cooling process, followed by further mixing.

The aqueous phase comprises water, and may further comprise an oleaginous base, and furthermore, may comprise a 1,2-alkanediol or glycerol, a fatty acid, polyethylene glycol, and other additives.

The heating temperatures of the aqueous compositions in the step 1) and the step 4) are each preferably 50° C. to 90° C., more preferably 60° C. to 90° C., for example, 70° C., or 80° C. The steps are preferably performed while stirring. Here, the heating (stirring) time in each of the steps depends on the lipid peptide compounds, the surfactants, and other ingredients that are contained in the aqueous composition, and depends on the amounts of these ingredients to be contained, but, typically, the heating (stirring) time is about 5 minutes to 50 minutes. Through the steps, the aqueous composition is uniformly dissolved.

The temperatures of heating the aqueous phase in the step 2) and the step 5) are each preferably 50° C. to 90° C., more preferably 60° C. to 90° C., for example, 70° C., or 80° C. In particular, in the case where the aqueous phase comprises other ingredients such as an oleaginous base, the heating of the aqueous phase is preferably performed while stirring. In the case where the aqueous phase comprises an oleaginous base, and furthermore comprises a 1,2-alkanediol or glycerol, a fatty acid, polyethylene glycol, and other additives, heating (stirring) is preferably performed typically for about 5 minutes to about 50 minutes until these ingredients are uniformly dissolved or dispersed. Note that the temperature of heating the aqueous phase may be the same as the temperature of heating the aqueous composition.

Subsequently, in the step 3) and the step 6), the mixtures obtained in the respective previous steps are cooled to form a gel. At this time, the mixtures may be cooled while being stirred. In the case where the mixtures are cooled while being stirred, it is preferable that the mixtures are stirred until the cooling temperature reaches, for example, room temperature to 80° C., room temperature to 60° C., or, for example, about 60° C., and then, the stirring is stopped and the mixtures are left standing to cool. In particular, it is preferable that the stirring is stopped at 50° C., or lower, and the mixtures are left standing to cool.

In the case where the solid base material for skin external application contains an organic acid such as ascorbic acid, a step is included in which, during the step 6) (cooling process), a mixed solution of water and the organic acid is added to the mixture, followed by further mixing.

In the present step, the mixed solution of water and the organic acid to be added preferably has the same or approximately the same temperature as that of the mixture to which the mixed solution is added, whereby uniform mixing can be achieved. The mixed solution may contain a 1,2-alkanediol or glycerol, an oleaginous base, a fatty acid, polyethylene glycol, and other additives, if desired, and may be heated (stirred) at a suitable temperature until these ingredients are uniformly dissolved or dispersed.

For example, when the mixture is stirred in the step 6) and the liquid temperature thereof reaches about 60° C., a mixed solution of water and an organic acid that has a liquid temperature of about 60° C. is added to the mixture, and the mixture is further stirred such that the mixed system is made uniform, and then, preferably, the stirring is stopped, and the mixture is left standing to cool, whereby a gel (a solid base material for skin external application) can be obtained.

Also in the solid base material for skin external application that is obtained by using the aqueous composition, the amount of water to be contained is preferably 60% by mass or more and less than 95% by mass with respect to the total mass of the solid base material for skin external application.

EXAMPLES

The present invention will now be described in detail with reference to Examples and Test Examples, but the present invention is not limited to these Examples.

Synthesis Example 1: Synthesis of Lipid Peptide (N-Palmitoyl-Gly-His)

A lipid peptide used as a gelator in Examples was synthesized in accordance with a method described below.

Into a 4-necked 500-mL flask, 14.2 g (91.6 mmol) of histidine, 30.0 g (91.6 mmol) of N-palmitoyl-Gly-methyl, and 300 g of toluene were charged, and 35.3 g (183.2 mmol) of a sodium methoxide 28% methanol solution was added thereto as a base. The mixture was heated to 60° C. in an oil bath, and stirred for 1 hour. Then, the oil bath was removed, and the solution was allowed to cool to 25° C. To the solution, 600 g of acetone was added to perform reprecipitation, and the resulting solid was collected by filtration. The solid obtained here was dissolved in a mixed solution of 600 g of water and 750 g of methanol. To the solution, 30.5 ml (183.2 mmol) of 6N hydrochloric acid was added to neutralize the solution and precipitate a solid, and the solid was collected by filtration. Next, the obtained solid was dissolved in a mixed solution of 120 g of tetrahydrofuran and 30 g of water at 60° C., and 150 g of ethyl acetate was added thereto. The mixture was cooled from 60° C. to 30° C. Then, the precipitated solid was collected by filtration. Furthermore, the obtained solid was dissolved in a mixed solvent of 120 g of tetrahydrofuran and 60 g of acetonitrile. The solution was heated to 60° C., stirred for 1 hour, and then cooled, followed by filtration. The obtained solid was washed with 120 g of water, collected by filtration, and then was dried under reduced pressure to obtain 26.9 g of white crystals of the free form of N-palmitoyl-Gly-His (hereinafter, also simply referred to as Pal-GH) (yield 65%).

Example 1 to Example 4, Comparative Example 1 and Comparative Example 2

(Method for Preparing a Solid Base Material for Skin External Application)

In accordance with Table 1 below, the ingredients of Phase A were weighed out in a sample tube No. 5. The weighed-out Phase A was heated to 70° C., or higher to be dissolved uniformly. On the other hand, 5.0 g of water serving as Phase B was weighed out in another sample tube No. 5 and heated to 70° C., or higher. Subsequently, Phase A was added to and mixed with Phase B and stirred for about 30 seconds while being heated, and then, the mixture was left standing to cool.

(Method for Measuring Breaking Strength)

Using YAMADEN RHEONER II CREEP METER RE2-33005B (manufactured by Yamaden Co., Ltd.), the breaking strength was measured under the conditions of a measurement speed: 0.5 mm/second, a measurement distortion factor: 20%, a storing pitch: 0.10 second, and a jig: 30349-3.

Table 1 lists the obtained results.

TABLE 1

| Ingredient (g) | | Comparative Example 1 | Comparative Example 2 | Example 1 | Example 2 | Example 3 | Example 4 |
|---|---|---|---|---|---|---|---|
| Phase A | Pal-GH | 0.50 | 0.50 | 0.50 | 0.50 | 0.50 | 0.50 |
| | 1,2-hexanediol [*1] | | 0.20 | 0.20 | 0.20 | 0.20 | 0.20 |
| | NIKKOL Lecinol LL-20 [*2] | | | 0.10 | | | |
| | NIKKOL Lecinol S-10EX [*3] | | | | 0.25 | | |
| | NIKKOL BL4.2 [*4] | | | | | 0.40 | 0.40 |
| | Stearic acid [*5] | | 0.05 | 0.05 | 0.05 | 0.05 | |
| | Water | 4.5 | 1.75 | 4.15 | 4.00 | 3.85 | 3.90 |
| Phase B | Water | 5.0 | 7.50 | 5.00 | 5.00 | 5.00 | 5.00 |
| Breaking strength [×10$^5$ Pa] | | N.D. [*6] | N.D. [*6] | 1.10 | 0.99 | 1.34 | 1.34 |

[*1] manufactured by I.T.O. Co., Ltd.
[*2] manufactured by Nikko Chemicals Co., Ltd.: hydrogenated enzymolyzed soybean phospholipid
[*3] manufactured by Nikko Chemicals Co., Ltd.: purified hydrogenated soybean phospholipid
[*4] manufactured by Nikko Chemicals Co., Ltd.: POE (4.2) lauryl ether
[*5] manufactured by Kao Corporation [Trade name: Lunac S-98]
[*6] lower than detection limit (breaking stress was not detectable)

Example 5 to Example 9

(Method for Preparing a Solid Base Material for Skin External Application)

In accordance with Table 2 below, the ingredients of Phase A were weighed out in a sample tube No. 5. The weighed-out Phase A was heated to 70° C., or higher to be dissolved uniformly. On the other hand, each of the ingredients of Phase B was weighed out in another sample tube No. 5 and heated to 70° C., or higher. Subsequently, Phase A was added to and mixed with Phase B and stirred for about 30 seconds while being heated, and then, the mixture was stirred and cooled to 60° C. After the temperature of the mixture reached 60° C., the mixture was left standing to cool.

The breaking strength was measured in the same manner as the above-described (Method for measuring breaking strength).

Table 2 lists the obtained results.

TABLE 2

| Ingredient (g) | | Example 5 | Example 6 | Example 7 | Example 8 | Example 9 |
|---|---|---|---|---|---|---|
| Phase A | Pal-GH | 0.50 | 0.50 | 0.50 | 0.50 | 0.50 |
| | 1,2-hexanediol [*1] | 0.20 | 0.20 | 0.20 | 0.20 | 0.20 |
| | NIKKOL BL4.2 [*4] | 0.40 | 0.40 | 0.40 | 0.40 | 0.40 |
| | Stearic acid [*5] | 0.05 | 0.05 | 0.05 | 0.05 | 0.05 |
| | Water | 3.85 | 3.85 | 3.85 | 3.85 | 3.85 |
| Phase B | Mineral oil | 2.00 | 5.00 | | | |
| | NIKKOL Trifat s-308 [*7] | | | 2.00 | | |
| | KF-995 [*8] | | | | 2.00 | 5.00 |
| | Water | 3.00 | | 3.00 | 3.00 | |
| Breaking strength [×10$^5$ Pa] | | 0.70 | 1.40 | 0.84 | 0.42 | 1.20 |
| pH | | 5.0 | 5.0 | 5.0 | 5.0 | 5.0 |

[*1] manufactured by I.T.O. Co., Ltd.
[*4] manufactured by Nikko Chemicals Co., Ltd.: POE (4.2) lauryl ether
[*5] manufactured by Kao Corporation [Trade name: Lunac S-98]
[*7] manufactured by Nikko Chemicals Co., Ltd.: glyceryl tri-2-ethylhexanoate
[*8] manufactured by Shin-Etsu Chemical Co., Ltd.: cyclopentasiloxane As listed in Table 1 and Table 2, the solid base materials for skin external application of Example 1 to Example 9 each had a breaking strength of 0.42×10$^5$ Pa to 1.40×10$^5$ Pa, particularly had a strength required as a stick-shaped base material.

On the contrary, in Comparative Example 1, which contained neither a 1,2-alkanediol nor a surfactant, and Comparative Example 2, which contained no surfactant, breaking stress was not detected, and the result reveals that the solid base materials for skin external application of Comparative Example 1 and Comparative Example 2 had an insufficient strength as a stick-shaped base material.

Example 10 to Example 15

In accordance with Table 3 below, the ingredients of Phase A were weighed out in a sample tube No. 5. The weighed-out Phase A was heated to 70° C., or higher to be dissolved uniformly. On the other hand, the ingredients of Phase B were weighed out in another sample tube No. 5 and heated to 70° C., or higher. Subsequently, Phase A was added to and mixed with Phase B and stirred for about 30 seconds while being heated, and then, the mixture was stirred and cooled to 60° C. After the temperature of the mixture reached 60° C., the mixture was left standing to cool. Note that the glycerol in Phase B of Example 14 was added as a moisturizer and a texture improver.

The breaking strength was measured in the same manner as the above-described (Method for measuring breaking strength).

Table 3 lists the obtained results.

TABLE 3

|  | Ingredient (g) | Example 10 | Example 11 | Example 12 | Example 13 | Example 14 | Example 15 |
|---|---|---|---|---|---|---|---|
| Phase A | Pal-GH | 0.500 | 0.500 | 0.500 | 0.500 | 0.500 | 0.500 |
|  | 1,2-pentanediol *1 | 0.500 |  |  |  |  |  |
|  | Stearic acid *5 | 0.075 | 0.025 | 0.025 | 0.025 | 0.025 | 0.025 |
|  | NIKKOL Decaglyn 2-ISV *9 | 0.075 |  |  |  |  |  |
|  | NIKKOL Lecinol SH50 *10 |  | 0.500 | 0.500 | 0.500 | 0.500 | 0.500 |
|  | Water | 1.350 | 1.475 | 1.475 | 1.475 | 1.475 | 1.475 |
| Phase B | Water | 7.500 | 7.500 | 6.500 | 6.500 | 6.500 | 6.500 |
|  | Mineral oil |  |  | 1.000 |  |  |  |
|  | Squalane |  |  |  | 1.000 |  |  |
|  | Glycerol |  |  |  |  | 1.000 |  |
|  | 1,3-butanediol |  |  |  |  |  | 1.000 |
|  | Breaking strength [×10$^5$ Pa] | 5.0 | 4.5 | 1.8 | 3.2 | 5.2 | 3.9 |

*1 manufactured by I.T.O. Co., Ltd.
*5 manufactured by Kao Corporation [Trade name: Lunac S-98]
*9 manufactured by Nikko Chemicals Co., Ltd.: polyglyceryl-10 diisostearate
*10 manufactured by Nikko Chemicals Co., Ltd.: hydrogenated soybean phospholipid 50% glycerol solution As listed in Table 3, the solid base materials for skin external application of Example 10 to Example 15 each had a high breaking strength of $1.8 \times 10^5$ Pa to $5.2 \times 10^5$ Pa.

Examples 16 and 17

In accordance with Table 4 below, the ingredients of Phase A were weighed out in a Maruemu sample tube No. 3. The weighed-out Phase A was heated in a water bath (set temperature: 85° C.) to be dissolved uniformly. On the other hand, the ingredients of Phase B were weighed out in another Maruemu sample tube No. 5 having a stirrer chip put therein, and the weighed-out Phase B was heated in a water bath (set temperature: 85° C.). Phase A was added to Phase B, and stirring and cooling were started and continued until the liquid temperature of the mixture reached about 60° C. On the other hand, the ingredients of Phase C were weighed out in another sample tube No. 5 and heated so that the liquid temperature of Phase C reached about 60° C. At the time when the liquid temperature of Phase A+Phase B reached 60° C., Phase C having a liquid temperature of about 60° C. was added thereto, and the mixture was stirred for about 30 seconds, and then left standing to cool.

The breaking strength was measured in the same manner as the above-described (Method for measuring breaking strength).

Table 4 lists the obtained results.

TABLE 4

|  | Ingredient (g) | Example 16 | Example 17 |
|---|---|---|---|
| Phase A | Pal-GH | 0.500 | 0.500 |
|  | NIKKOL Lecinol SH50*10 | 0.500 | 0.500 |
|  | Stearic acid*5 | 0.025 | 0.025 |
|  | Water | 1.475 | 1.475 |
| Phase B | Water | 5.000 | 5.000 |
| Phase C | Ascorbic acid | 0.500 | 1.000 |
|  | Water | 2.000 | 1.500 |
|  | Breaking strength [×10$^5$ Pa] | 2.4 | 2.1 |

*5 manufactured by Kao Corporation [Trade name: Lunac S-98]
*10 manufactured by Nikko Chemicals Co., Ltd.: hydrogenated soybean phospholipid As listed in Table 4, the solid base materials for skin external application of Example 16 and Example 17 each had a high breaking strength of $2.1 \times 10^5$ Pa to $2.4 \times 10^5$ Pa although 5% by mass (Example 16) and 10% by mass (Example 17) of ascorbic acid were added with respect to the total mass of the respective solid base materials for skin external application.

Example 18, and Reference Example 1 to Reference Example 3

In accordance with Table 5 below, the ingredients of Phase A were weighed out in a Maruemu sample tube No. 7. The weighed-out Phase A was heated and stirred in a water bath (set temperature: 80° C.) until the liquid temperature of Phase A reached 80° C., whereby Phase A was dissolved uniformly. Note that, at this time, a magnetic stirrer was used for the stirring. On the other hand, the ingredients of Phase B were weighed out in another Maruemu sample tube No. 7 having a stirrer chip put therein, and the weighed-out Phase B was heated and stirred in a water bath (set temperature: 80° C.) until the liquid temperature of Phase B reached 80° C. Phase A was added to Phase B, and the mixture was heated and stirred at the above-mentioned set temperature for one minute. The sample tube having Phase A+Phase B put therein was removed from the water bath, and cooling was started. Upon the start of the cooling, the magnetic stirrer was removed out, and subsequent stirring was manually performed using a spatula until the liquid temperature of the mixture reached 60° C.

When the liquid temperature reached 60° C., a metal container (a lip stick container having an inside diameter of φ9.5 mm, manufactured by HIDAN CO., LTD., and including a container body and a lid attached to cover the whole of the body) was made ready and filled up with the mixture. Immediately after that, an opening portion of the container body was sealed up with an aluminum tape so as to seal the mixture filled thereinto, and furthermore, a capsule was put from above as a temporary lid so as to cover the container body, whereby a filled and sealed sample was produced. Four of such filled and sealed samples (N-1 to N-4) were produced for every Example, and then, left standing to cool at room temperature for 30 minutes.

After the samples were left standing still for 30 minutes, the capsule serving as a temporary lid was removed from the container, and a lid was attached thereto.

After the metal container was covered with the lid, the mass of the filled metal container was measured. Then, from the measured mass, the mass of the metal container (including the container body, the lid, and the aluminum tape) measured in advance was deducted to calculate the mass of the filled sample (the mass of the sample at the time of preparation). Subsequently, the filled and sealed sample covered with the lid was stored for 2 weeks in a thermostat oven set at 45° C., and the mass was measured again to calculate the mass of the filled sample after the 2-week storage (the mass of the sample after the storage). The mass loss rate after the 2-week storage was calculated by the formula below. Table 5 lists the obtained results. A lower mass loss rate indicates a lower mass loss of the sample, suggesting higher temporal stability of the sample.

Mass Loss Rate (%)=100−{[Mass of Sample after Storage/Mass of Sample at the Time of Preparation]×100}

As listed in Table 5, the results revealed that the mass loss rate of the polyethylene-glycol-containing solid base material for skin external application of Example 18 was lower and that the temporal stability thereof was higher than those of Reference Example 1 to Reference Example 3.

Example 19 to Example 22

In accordance with Table 6 below, the ingredients of Phase A were weighed out in a sample tube No. 5. The weighed-out Phase A was heated to 70° C., or higher to be dissolved uniformly. On the other hand, 5.0 g of water serving as Phase B was weighed out in another sample tube No. 5 and heated to 70° C., or higher. Subsequently, Phase A was added to and mixed with Phase B and stirred for about 30 seconds while being heated, and then, the mixture was left standing to cool.

The breaking strength was measured in the same manner as the above-described (Method for measuring breaking strength).

TABLE 5

| | Ingredient (g) | Example 18 | Reference Example 1 | Reference Example 2 | Reference Example 3 |
|---|---|---|---|---|---|
| Phase A | Pal-GH | 2.50 | 1.00 | 1.00 | 1.00 |
| | 1,2-hexanediol*[1] | 1.00 | 0.40 | 0.40 | 0.40 |
| | NIKKOL BL4.2*[4] | 2.00 | 0.80 | 0.80 | 0.80 |
| | Stearic acid*[5] | 0.25 | 0.10 | 0.10 | 0.10 |
| | Water | 19.25 | 7.70 | 7.70 | 7.70 |
| Phase B | Water | 23.50 | 10.00 | 8.00 | 8.00 |
| | Glycerol*[1] | | | 2.00 | |
| | 1,3-butanediol*[1] | | | | 2.00 |
| | Polyethylene glycol*[11] | 1.50 | | | |
| Mass loss rate (%) | N-1 | 0.30 | 0.50 | 0.44 | 0.47 |
| | N-2 | 0.36 | 0.55 | 0.46 | 0.47 |
| | N-3 | 0.33 | 0.49 | 0.57 | 0.47 |
| | N-4 | 0.33 | 0.52 | 0.47 | 0.50 |
| | Average | 0.33 | 0.52 | 0.49 | 0.47 |

*[1]manufactured by I.T.O. Co., Ltd.
*[4]manufactured by Nikko Chemicals Co., Ltd.: POE (4.2) lauryl ether
*[5]manufactured by Kao Corporation [Trade name: Lunac S-98]
*[11]manufactured by NOF CORPORATION [Trade name: PEG#4000]

Table 6 lists the obtained results.

TABLE 6

| | Ingredient (g) | Example 19 | Example 20 | Example 21 | Example 22 |
|---|---|---|---|---|---|
| Phase A | Pal-GH | 0.50 | 0.50 | 0.50 | 0.50 |
| | 1,2-hexanediol*[1] | 0.20 | 0.20 | 0.20 | 0.20 |
| | EMULGEN 104P*[12] | 0.40 | | | |
| | EMANON 1112*[13] | | 0.40 | | |
| | EMULGEN 1108*[14] | | | 0.40 | |
| | EMULGEN LS-106*[15] | | | | 0.40 |
| | Stearic acid*[5] | 0.05 | 0.05 | 0.05 | 0.05 |
| | Water | 3.85 | 3.85 | 3.85 | 3.85 |
| Phase B | Water | 5.00 | 5.00 | 5.00 | 5.00 |
| | Breaking strength [×$10^5$ Pa] | 1.50 | 1.60 | 0.45 | 2.01 |

*[1]manufactured by I.T.O. Co., Ltd.
*[5]manufactured by Kao Corporation [Trade name: Lunac S-98]
*[12]manufactured by Kao Corporation: polyoxyethylene (4) lauryl ether
*[13]manufactured by Kao Corporation: polyoxyethylene (12) monolaurate
*[14]manufactured by Kao Corporation: polyoxyethylene (8) alkyl ether
*[15]manufactured by Kao Corporation: polyoxyethylene polyoxypropylene alkyl ether As listed in Table 6, the solid base materials for skin external application of Example 19 to Example 22 each had a breaking strength of $0.45 \times 10^5$ Pa to $2.01 \times 10^5$ Pa, particularly had a strength required as a stick-shaped base material.

The invention claimed is:

1. A solid base material for skin external application, the solid base material comprising:
- at least one surfactant selected from the group consisting of ethylene glycol alkyl ether, phospholipid, polyglycerol fatty acid esters, and polyoxyethylene polyoxypropylene alkyl ether;
- one selected from a 1,2-alkanediol or glycerol;
- at least one fatty acid;
- water; and
- a lipid peptide compound including at least one of compounds of Formulae (1) to (3) or pharmaceutically usable salts of the compound:

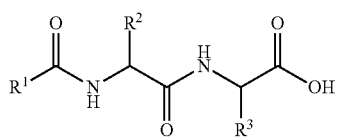

(1)

where $R^1$ is a $C_{9-23}$ aliphatic group; $R^2$ is a hydrogen atom, or a $C_{1-4}$ alkyl group that may have a $C_1$ or $C_2$ branched chain; and $R^3$ is a $-(CH_2)_n-X$ group, where n is a number from 1 to 4, and X is amino group, guanidino group, $-CONH_2$ group, or a 5-membered or 6-membered ring that may have 1 to 3 nitrogen atoms or a condensed heterocycle composed of 5-membered and 6-membered rings that may have 1 to 3 nitrogen atoms,

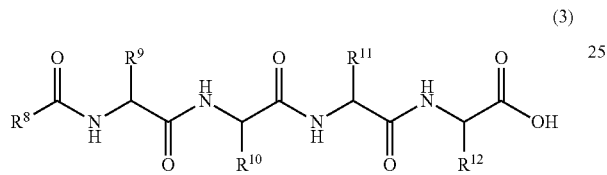

where $R^4$ is a $C_{9-23}$ aliphatic group; $R^5$ to $R^7$ are each independently a hydrogen atom, a $C_{1-4}$ alkyl group that may have a $C_1$ or $C_2$ branched chain, or a —$(CH_2)_n$—X group, where n is a number from 1 to 4, and X is amino group, guanidino group, —$CONH_2$ group, or a 5-membered or 6-membered ring that may have 1 to 3 nitrogen atoms or a condensed heterocycle composed of 5-membered and 6-membered rings that may have 1 to 3 nitrogen atoms,

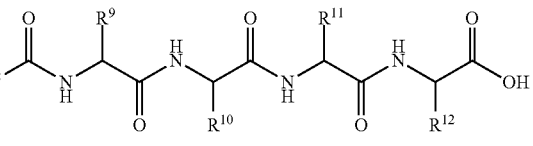

where $R^8$ is a $C_{9-23}$ aliphatic group; $R^9$ to $R^{12}$ are each independently a hydrogen atom, a $C_{1-4}$ alkyl group that may have a $C_1$ or $C_2$ branched chain, or a —$(CH_2)_n$—X group, where n is a number from 1 to 4, and X is amino group, guanidino group, —$CONH_2$ group, or a 5-membered or 6-membered ring that may have 1 to 3 nitrogen atoms or a condensed heterocycle composed of 5-membered and 6-membered rings that may have 1 to 3 nitrogen atoms.

2. The solid base material for skin external application according to claim 1, further comprising at least one oleaginous base.

3. The solid base material for skin external application according to claim 1, further comprising at least one organic acid.

4. The solid base material for skin external application according to claim 1, wherein the fatty acid is stearic acid.

5. The solid base material for skin external application according to claim 3, wherein the organic acid is ascorbic acid.

6. The solid base material for skin external application according to claim 1, further comprising polyethylene glycol.

7. The solid base material for skin external application according to claim 1, wherein the solid base material is used for cosmetics or pharmaceuticals.

8. The solid base material for skin external application according to claim 1, wherein the solid base material has a shape of a stick.

9. An aqueous composition comprising:
   at least one surfactant selected from the group consisting of ethylene glycol alkyl ether, phospholipid, polyglycerol fatty acid esters, and polyoxyethylene polyoxypropylene alkyl ether;
   one selected from a 1,2-alkanediol or glycerol;
   at least one fatty acid;
   water; and
   a lipid peptide compound including at least one of compounds of the Formulae (1) to (3) or pharmaceutically usable salts of the compound:

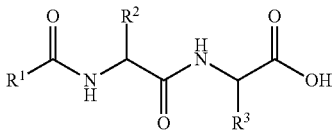

where $R^1$ is a $C_{9-23}$ aliphatic group; $R^2$ is a hydrogen atom, or a $C_{1-4}$ alkyl group that may have a $C_1$ or $C_2$ branched chain; and $R^3$ is a —$(CH_2)_n$—X group, where n is a number from 1 to 4, and X is amino group, guanidino group, —$CONH_2$ group, or a 5-membered or 6-membered ring that may have 1 to 3 nitrogen atoms or a condensed heterocycle composed of 5-membered and 6-membered rings that may have 1 to 3 nitrogen atoms,

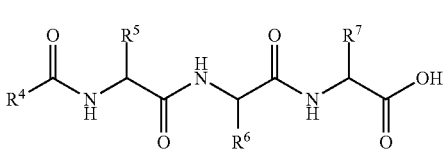

where $R^4$ is a $C_{9-23}$ aliphatic group; $R^5$ to $R^7$ are each independently a hydrogen atom, a $C_{1-4}$ alkyl group that may have a $C_1$ or $C_2$ branched chain, or a —$(CH_2)_n$—X group, where n is a number from 1 to 4, and X is amino group, guanidino group, —$CONH_2$ group, or a 5-membered or 6-membered ring that may have 1 to 3 nitrogen atoms or a condensed heterocycle composed of 5-membered and 6-membered rings that may have 1 to 3 nitrogen atoms,

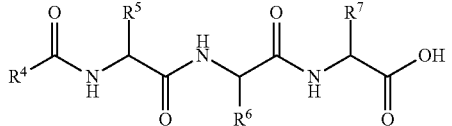

where $R^8$ is a $C_{9-23}$ aliphatic group; $R^9$ to $R^{12}$ are each independently a hydrogen atom, a $C_{1-4}$ alkyl group that may have a $C_1$ or $C_2$ branched chain, or a —$(CH_2)_n$—X group, where n is a number from 1 to 4, and X is amino group, guanidino group, —$CONH_2$ group, or a 5-membered or 6-membered ring that may have 1 to 3 nitrogen atoms or a condensed heterocycle composed of 5-membered and 6-membered rings that may have 1 to 3 nitrogen atoms.

10. The aqueous composition according to claim 9, wherein the aqueous composition is a premix for the preparation of a solid base material for skin external application.

11. A method for producing the solid base material for skin external application as claimed in claim 1, the method comprising the steps of:
    heating an aqueous composition at room temperature or higher and less than 100° C., the aqueous composition comprising:
    a surfactant;
    water; and a lipid peptide compound including at least one of compounds of the Formulae (1)' to (3)' or pharmaceutically usable salts of the compound:

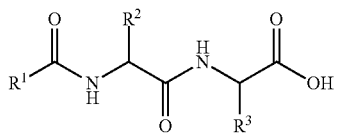

(1)' where $R^1$ is a $C_{9-23}$ aliphatic group; $R^2$ is a hydrogen atom, or a $C_{1-4}$ alkyl group that may have a $C_1$ or $C_2$ branched chain; and $R^3$ is a —(CH$_2$)$_n$—X group, where n is a number from 1 to 4, and X is amino group, guanidino group, —CONH$_2$ group, or a 5-membered or 6-membered ring that may have 1 to 3 nitrogen atoms or a condensed heterocycle composed of 5-membered and 6-membered rings that may have 1 to 3 nitrogen atoms,

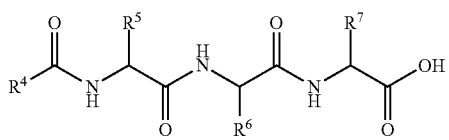

(2)' where $R^4$ is a $C_{9-23}$ aliphatic group; $R^5$ to $R^7$ are each independently a hydrogen atom, a $C_{1-4}$ alkyl group that may have a $C_1$ or $C_2$ branched chain, or a —(CH$_2$)$_n$—X group, where n is a number from 1 to 4, and X is amino group, guanidino group, —CONH$_2$ group, or a 5-membered or 6-membered ring that may have 1 to 3 nitrogen atoms or a condensed heterocycle composed of 5-membered and 6-membered rings that may have 1 to 3 nitrogen atoms,

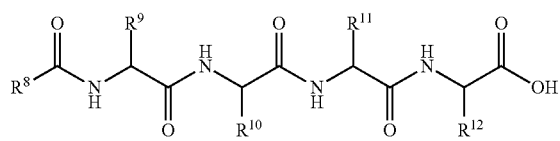

(3)' where $R^8$ is a $C_{9-23}$ aliphatic group; $R^9$ to $R^{12}$ are each independently a hydrogen atom, a $C_{1-4}$ alkyl group that may have a $C_1$ or $C_2$ branched chain, or a —(CH$_2$)$_n$—X group, where n is a number from 1 to 4, and X is amino group, guanidino group, —CONH$_2$ group, or a 5-membered or 6-membered ring that may have 1 to 3 nitrogen atoms or a condensed heterocycle composed of 5-membered and 6-membered rings that may have 1 to 3 nitrogen atoms;
adding the heated aqueous composition to an aqueous phase heated at room temperature or higher and less than 100° C., followed by mixing; and
cooling the resultant mixture to form a gel.

12. The production method according to claim 11, wherein the aqueous phase contains at least one oleaginous base.

13. The production method according to claim 11, wherein the aqueous phase contains polyethylene glycol.

14. A method for producing the solid base material for skin external application as claimed in claim 3, the method comprising the steps of:
heating an aqueous composition at room temperature or higher and less than 100° C., the aqueous composition comprising:
a surfactant;
water; and
a lipid peptide compound including at least one of compounds of the Formulae (1)' to (3)' or pharmaceutically usable salts of the compound:

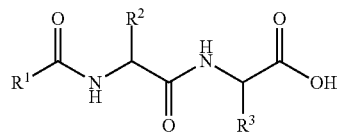

(1)' where $R^1$ is a $C_{9-23}$ aliphatic group; $R^2$ is a hydrogen atom, or a $C_{1-4}$ alkyl group that may have a $C_1$ or $C_2$ branched chain; and $R^3$ is a —(CH$_2$)$_n$—X group, where n is a number from 1 to 4, and X is amino group, guanidino group, —CONH$_2$ group, or a 5-membered or 6-membered ring that may have 1 to 3 nitrogen atoms or a condensed heterocycle composed of 5-membered and 6-membered rings that may have 1 to 3 nitrogen atoms,

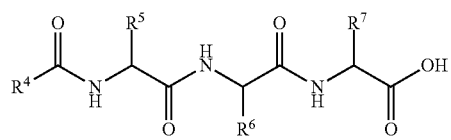

(2)' where $R^4$ is a $C_{9-23}$ aliphatic group; $R^5$ to $R^7$ are each independently a hydrogen atom, a $C_{1-4}$ alkyl group that may have a $C_1$ or $C_2$ branched chain, or a —(CH$_2$)$_n$—X group, where n is a number from 1 to 4, and X is amino group, guanidino group, —CONH$_2$ group, or a 5-membered or 6-membered ring that may have 1 to 3 nitrogen atoms or a condensed heterocycle composed of 5-membered and 6-membered rings that may have 1 to 3 nitrogen atoms,

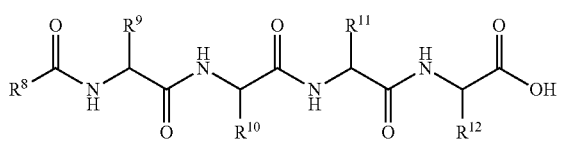

(3)' where $R^8$ is a $C_{9-23}$ aliphatic group; $R^9$ to $R^{12}$ are each independently a hydrogen atom, a $C_{1-4}$ alkyl group that may have a $C_1$ or $C_2$ branched chain, or a —(CH$_2$)$_n$—X group, where n is a number from 1 to 4, and X is amino group, guanidino group, —CONH$_2$ group, or a 5-membered or 6-membered ring that may have 1 to 3 nitrogen atoms or a condensed heterocycle composed of 5-membered and 6-membered rings that may have 1 to 3 nitrogen atoms;
adding the heated aqueous composition to an aqueous phase heated at room temperature or higher and less than 100° C., followed by mixing;
cooling the resultant mixture to form a gel; and
adding a mixed solution of water and an organic acid to the mixture during the cooling process, followed by further mixing.

15. The production method according to claim 14, wherein the aqueous phase contains at least one oleaginous base.

\* \* \* \* \*

```
                         SEQUENCE LISTING

<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: synthetic compound
<220> FEATURE:
<221> NAME/KEY: LIPID
<222> LOCATION: (1)..(1)
<223> OTHER INFORMATION: lauroyl moiety bonded to N-terminal glycine
      residue

<400> SEQUENCE: 1

Gly Gly Gly His
1

<210> SEQ ID NO 2
<211> LENGTH: 4
<212> TYPE: PRT
<213> ORGANISM: Artificial Sequence
<220> FEATURE:
<223> OTHER INFORMATION: synthetic compound
<220> FEATURE:
<221> NAME/KEY: LIPID
<222> LOCATION: (1)..(1)
<223> OTHER INFORMATION: myristoyl moiety bonded to N-terminal glycine
      residue

<400> SEQUENCE: 2

Gly Gly Gly His
1

<210> SEQ ID NO 3
<211> LENGTH: 4
<212> TYPE: PRT
<213> ORGANISM: Artificial Sequence
<220> FEATURE:
<223> OTHER INFORMATION: synthetic compound
<220> FEATURE:
<221> NAME/KEY: LIPID
<222> LOCATION: (1)..(1)
<223> OTHER INFORMATION: palmitoyl moiety bonded to N-terminal glycine
      residue

<400> SEQUENCE: 3

Gly Gly Gly His
1

<210> SEQ ID NO 4
<211> LENGTH: 4
<212> TYPE: PRT
<213> ORGANISM: Artificial Sequence
<220> FEATURE:
<223> OTHER INFORMATION: synthetic compound
<220> FEATURE:
<221> NAME/KEY: LIPID
<222> LOCATION: (1)..(1)
<223> OTHER INFORMATION: palmitoyl moiety bonded to N-terminal glycine
      residue
```

```
<400> SEQUENCE: 4

Gly Gly His Gly
1

<210> SEQ ID NO 5
<211> LENGTH: 4
<212> TYPE: PRT
<213> ORGANISM: Artificial Sequence
<220> FEATURE:
<223> OTHER INFORMATION: synthetic compound
<220> FEATURE:
<221> NAME/KEY: LIPID
<222> LOCATION: (1)..(1)
<223> OTHER INFORMATION: palmitoyl moiety bonded to N-terminal glycine
      residue

<400> SEQUENCE: 5

Gly His Gly Gly
1

<210> SEQ ID NO 6
<211> LENGTH: 4
<212> TYPE: PRT
<213> ORGANISM: Artificial Sequence
<220> FEATURE:
<223> OTHER INFORMATION: synthetic compound
<220> FEATURE:
<221> NAME/KEY: LIPID
<222> LOCATION: (1)..(1)
<223> OTHER INFORMATION: palmitoyl moiety bonded to N-terminal histidine
      residue

<400> SEQUENCE: 6

His Gly Gly Gly
1

<210> SEQ ID NO 7
<211> LENGTH: 4
<212> TYPE: PRT
<213> ORGANISM: Artificial Sequence
<220> FEATURE:
<223> OTHER INFORMATION: synthetic compound
<220> FEATURE:
<221> NAME/KEY: LIPID
<222> LOCATION: (1)..(1)
<223> OTHER INFORMATION: stearoyl moiety bonded to N-terminal glycine
      residue

<400> SEQUENCE: 7

Gly Gly Gly His
1
```